(12) United States Patent
Spetz et al.

(10) Patent No.: US 10,626,401 B2
(45) Date of Patent: Apr. 21, 2020

(54) SINGLE-STRANDED OLIGONUCLEOTIDES FOR USE IN THE MEDICAL TREATMENT OF SKIN DISORDERS

(71) Applicants: Anna-Lena Spetz, Bromma (SE); Peter Jarver, Stockholm (SE); Annette Skold, Sundsvall (SE)

(72) Inventors: Anna-Lena Spetz, Bromma (SE); Peter Jarver, Stockholm (SE); Annette Skold, Sundsvall (SE)

(73) Assignee: TIRMED PHARMA AB, Bromma (SE)

( * ) Notice: Subject to any disclaimer, the term of this patent is extended or adjusted under 35 U.S.C. 154(b) by 0 days.

(21) Appl. No.: 15/736,020

(22) PCT Filed: Jun. 14, 2016

(86) PCT No.: PCT/EP2016/063596
§ 371 (c)(1),
(2) Date: Dec. 13, 2017

(87) PCT Pub. No.: WO2016/202779
PCT Pub. Date: Dec. 22, 2016

(65) Prior Publication Data
US 2018/0142246 A1 May 24, 2018

(30) Foreign Application Priority Data
Jun. 15, 2015 (SE) ...................................... 1550814

(51) Int. Cl.
| C07H 21/04 | (2006.01) |
| C12N 15/117 | (2010.01) |
| A61K 45/06 | (2006.01) |
| A61K 31/7125 | (2006.01) |
| A61P 17/00 | (2006.01) |

(52) U.S. Cl.
CPC ........ *C12N 15/117* (2013.01); *A61K 31/7125* (2013.01); *A61K 45/06* (2013.01); *A61P 17/00* (2018.01); *C12N 2310/17* (2013.01); *C12N 2310/315* (2013.01); *C12N 2310/321* (2013.01); *C12N 2310/346* (2013.01)

(58) Field of Classification Search
None
See application file for complete search history.

(56) References Cited

U.S. PATENT DOCUMENTS

| 7,807,803 B2 | 10/2010 | Krieg | |
| 8,101,345 B1 * | 1/2012 | Senn | ..................... C12N 15/111 435/6.1 |
| 2008/0299138 A1 | 12/2008 | Duffy et al. | |

FOREIGN PATENT DOCUMENTS

| WO | 2008/147956 A2 | 12/2008 |
| WO | 2009/082448 A2 | 7/2009 |

OTHER PUBLICATIONS

Adar, Tomer et al., "From airway inflammation to inflammatory bowel disease: Eotaxin-1, a key regulatory of intestinal inflammation", Clinical Immunology, 153: 199-208 (2014).
Ali, Syed Raza et al., "Siglec-5 and Siglec-14 are polymorphic paired receptors that modulate neutrophil and amnion signaling responses to group B *Streptococcus*", J. Exp. Med., 211(6): 1231-1242 (2014).
An, Hongyan et al., "Soluble LILRA3, a Potential Natural Antiinflammatory Protein, is Increased in Patients with Rheumatoid Arthritis and is Tightly Regulated by Interleukin 10, Tumor Necrosis Factor-α, and Interferon-γ", J. Rheumatol., 37: 1596-606 (2010).
Antonelli, Alessandro et al., "Chemokine (C-X-C motif) ligand (CXCL) 10 in autoimmune diseases", Autoimmunity Reviews, 13: 272-280 (2014).
Banchereau, Jacques et al., "Immunoglobulin-like transcript receptors on human dermal CD14+ dendritic cells act as a CD8-antagonist to control cytotoxic T cell printing", PNAS, 109(46): 18885-18890 (2012).
Bancherau, Jacques et al., "Dendritic cells and the control of immunity", Nature, 392: 245-252 (1998).
Beattie, P.E. et al., "An audit of the impact of a consultation with a paediatric dermatology team on quality of life in infants with atopic eczema and their families: further validation of the Infants' Dermatitis Quality of Life Index and Dermatitis Family Impact score", British Journal of Dermatology, 155: 1249-1255 (2006).
Biedermann, Tilo et al., "Regulation of T cell immunity in atopic dermatitis by microbes: the Yin and Yang of cutaneous inflammation", Front. Immunol., 6: 353 (2015).
Boniface, Katia et al., "Keratinocytes as targets for interleukin-10-related cytokines: a putative role in the pathogenesis of psoriasis", Eur. Cytokine Netw., 16: 309-19 (2005).
Cao, Wei et al., "Plasmacytoid dendritic cell-specific receptor ILT7-FceRIγ inhibits Toll-like receptor-induced interferon production", JEM, 203: 1399-1405 (2006).
Caskey, Marina et al., "Synthetic double-stranded RNA induces innate immune responses similar to a live viral vaccine in humans", J. Exp. Med., 208(12): 2357-2366 (2011).
Chang, C.C. et al., "Tolerization of dendritic cells by Ts cells: the crucial role of inhibitory receptors ILT3 and ILT4", 3(3): 237-243 (2002).
Colonna, Marco et al., "A Common Inhibitory Receptor for Major Histocompatibility Complex Class I Molecules on Human Lymphoid and Myelomonocytic Cells", J. Exp. Med., 186(11): 1809-1818 (1997).

(Continued)

*Primary Examiner* — Kimberly Chong
(74) *Attorney, Agent, or Firm* — Robert C. Netter, Jr.; Dann, Dorfman, Herrell & Skillman

(57) ABSTRACT

The invention relates to non-CpG single-stranded oligonucleotides (ssONs) for use in the treatment or prophylaxis of disorders of the skin and/or subcutaneous tissue, including pruritus, in a suitable formulation or in combination with other immunomodulatory treatments. The said ssONs have a length of at least 25 nucleotides and are stabilized by phosphorothioate internucleotide linkages and/or 2'-O-Methyl modifications.

14 Claims, 20 Drawing Sheets

Specification includes a Sequence Listing.

(56) References Cited

OTHER PUBLICATIONS

Deleavey, Glen F. et al., "Designing Chemically Modified Oligonucleotides for Targeted Gene Silencing", Chemistry & Biology, 19: 937-954 (2012).
Dorn, Annette et al., "Oligonucleotides Suppress IL-8 in Skin Keratinocytes In Vitro and Offer Anti-Inflammatory Properties in Vivo", Journal of Investigative Dermatology, 127: 846-854 (2007).
Duthie, Malcolm S. et al., "Use of defined TLR ligands as adjuvants within human vaccines", Immunological Reviews, 239: 178-196 (2011).
Hamilton, Jennifer D. et al., "Drug evaluation review: dupilumab in atopic dermatitis", Immunotherapy, 7(10): 1043-1058 (2015).
Hilbers, C.W. et al., "Structure and folding of DNA and RNA hairpins", Fresenius Z. Anal. Chem., 327: 70 (1987).
Jarver, Peter et al., "A Chemical View of Oligonucleotides for Exon Skipping and Related Drug Applications", Nucleic Acid Therapeutics, 24(1): 37-47 (2014).
Klechevsky, Eynav et al., "Functional Specializations of Human Epidermal Langerhans Cells and CD14+ Dermal Dendritic Cells", Immunity, 29: 497-510 (2008).
Lefebvre, Sylvie et al., "Ectodysplasin research—Where to next?", Seminars in Immunology, 26: 220-228 (2014).
Madden, Thomas, "The BLAST Sequence Analysis Tool", The NCBI Handbook [Internet], 2nd edition (2013).
Matsukura, Makoto et al., "Phosphorothioate analogs of oligodeoxynucleotides: Inhibitors of replication and cytopathic effects of human immunodeficiency virus", Proc. Natl. Acad. Sci. USA, 84: 7706-7710 (1987).
Nestle, F.O. et al., "Characterization of dermal dendritic cells obtained from normal human skin reveals phenotypic and functionally distinctive subsets", J. Immunol., 151: 6535-6545 (1993).
Mosser, David M. et al., "Interleukin-10: new perspectives on an old cytokine", Immunol. Rev., 226: 205-218 (2008).
Ranjith-Kumar, C.T. et al., "Single-Stranded Oligonucleotides Can Inhibit Cytokine Production Induced by Human Toll-Like Receptor 3", Molecular and Cellular Biology, 28(14): 4507-4519 (2008).
Rogoz, Katarzyna et al., "Identification of a Neuronal Receptor Controlling Anaphylaxis", Cell Reports, 14: 370-379 (2016).
Rogoz, Katarzyna et al., "Multimodal Use of Calcitonin Gene-Related Peptide and Substance P in Itch and Acute Pain Uncovered by the Elimination of Vesicular Glutamate Transporter 2 from Transient Receptor Potential Cation channel Subfamily V Member 1 Neurons", The Journal of Neuroscience, 34(42): 14055-14068 (2014).
Saeki, Hidehisa et al., "Clinical Practice Gujidelines for the Management of Atopic Dermatitis 2016", Journal of Dermatology, 43: 1117-1145 (2016).
Saxena, Ankit et al., "Interleukin-10 paradox: A potent immunoregulatory cytokine that has been difficult to harness for immunotherapy", Cytokine, 74: 27-34 (2015).
Serra, Martin J. et al., "RNA hairpin loop stability depends on closing base pair", Nucleic Acid Research, 21(16); 3845-3849 (1993).
Skold, Annette E. et al., "Single-stranded DNA oligonucleotides inhibit TLR3-mediated responses in human monocyte-derived dendritic cells and in vivo in cynomolgus macaques", Blood, 120: 768-777 (2012).
Slukvin, I.I. et al., "Cloning of rhesus monkey LILRs", Tissue antigens, 67: 331-337 (2006).
Soehnlein, Oliver et al., "Phagocyte partnership during the onset and resolution of inflammation", Nature Reviews. Immunology, 10: 427-439 (2010).
Tongaonkar, Prasad et al., "Rhesus macaque Θ-defensin RTD-1 inhibits proinflammatory cytokine secretion and gene expresion by inhibiting the activation of NF-κB and MAPK pathways", Journal of Leukocyte Biology, 98: 1061-1070 (2015).
Vallone, Peter M. et al., "Melting Studies of Short DNA Hairpins: Influence of Loop Sequence and Adjoining Base Pair Identity on Hairpin Thermodynamic Stabilty", Biopolymers, 50: 425-442 (1999).
Zaba, Lisa C. et al., "Normal human dermis contains distinct populations of CD11c+BDCA-1+ dendritic cells and CD163+ FFXIIIA+ macrophages", T. Clin. Invest. 117(2): 2517-2525 (2007).
Artificial DNA: Methods and Applications, CRC Press, 2003, Yury E. Khudyakov and Howard A. Fields eds.
World Health Organization. International Statistical Classification of Diseases and Related Health Problems, 10th Revision, vol. 2, Instruction Manual, 2010 Edition.
Vollmer, J., et al., "Oligodeoxynucleotides lacking CpG dinucleotides mediate Toll-like receptor 9 dependent T helper type 2 biased immune stimulation" Immunology (2004) 113:212-223.
Weber, C., et aL, "Toll-like receptor (TLR) 3 immune modulation by unformulatedsmall interfering RNA or DNA and the role of CD14 (in TLR-mediated effects)" Immunology (2012) 136:64-77.
Roberts, T.L., et al., "Cutting Edge: Species-Specific TLR9-Mediated Recognition of CpG and Non-CpG Phosphorothioate-Modified Oligonucleotides" J. Immunology (2005) 174: 605-608.
Krieg, A.M., et al., "Therapeutic potential of Toll-like receptor 9 activation" Nature Reviews (2006) 5:471-484.
Nazli, A., et al., "Differential induction of innate antiviral responses by TLR ligands against Herpes simplex virus, type 2, infection in primary genital epithelium of women" Antiviral Research (2009) 81:103-112.
Grimstad, O., et al., "Oligodeoxynucleotides inhibit Toll-like receptor 3 mediated cytotoxicity and CXCL8 release in keratinocytes" Experimental Dermatology (2011) 21:7-12.
Liu, T., et al., "TLR3 deficiency impairs spinal cord synaptic transmission, central sensitization, and pruritus in mice" J. Clin. Invest., (2012) 122(6):2195-2207.
Anonymous, "Toll-Like Receptors and Viral Infection—Review" (2005) [online] Retrieved from the Internet <URL: https://www.invivogen.com/review-tlr-viral-infection>.

* cited by examiner

SEQUENCE LISTING

```
<160> NUMBER OF SEQ ID NOS: 20

<210> SEQ ID NO 1
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 1
gtcgttttgt cgttttgtcg ttgttggtgg tggtg                          35

<210> SEQ ID NO 2
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 2
gaagttttga ggttttgaag ttgttggtgg tggtg                          35

<210> SEQ ID NO 3
<211> LENGTH: 35
<212> TYPE: DNA
<213> ORGANISM: Artificial sequence
```

```
<220> FEATURE:
<223> OTHER INFORMATION: Synthetic oligonucleotide

<400> SEQUENCE: 3
aaaattttaa aattttaaaa ttattaataa taata                          35

<210> SEQ ID NO 4
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 4
ggttttgaag ttgtt                                                15

<210> SEQ ID NO 5
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 5
caccaccacc aacaacttca aaacctcaaa acttc                          35

<210> SEQ ID NO 6
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 6
aaaaaaaaaa aaaaaaaaaa aaaaaaaaaa aaaaa                          35

<210> SEQ ID NO 7
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 7
tttttttttt tttttttttt tttttttttt ttttt                          35

<210> SEQ ID NO 8
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 8
cccccccccc cccccccccc cccccccccc ccccc                          35

<210> SEQ ID NO 9
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 9
gggggggggg gggggggggg gggggggggg ggggg                          35
```

```
<210> SEQ ID NO 10
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 10
ccctccccct ccctccccct ccctccccct ccct                              35

<210> SEQ ID NO 11
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 11
gggaagggaa gggaagggaa gggaagggaa gggaa                             35

<210> SEQ ID NO 12
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 12
gaagttttga ggttttgaag ttattggtgg tggtg                             35

<210> SEQ ID NO 13
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 13
agttttgagg ttttgaagtt gttggtggtg                                   30

<210> SEQ ID NO 14
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 14
agttttgagg ttttgaagtt attggtggtg                                   30

<210> SEQ ID NO 15
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 15
tttgaggttt tgaagttgtt ggtgg                                        25

<210> SEQ ID NO 16
<211> LENGTH: 25
<212> TYPE: DNA
<213> ORGANISM: Artificial sequence
<220> FEATURE:
<223> OTHER INFORMATION: Synthetic oligonucleotide
```

```
<400> SEQUENCE: 16
tttgaggttt tgaagttatt ggtgg                                          25

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
tgaggttttg aagttgttgg                                                20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
tgaggttttg aagttattgg                                                20

<210> SEQ ID NO 19
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 19
gaagttttga ggttttgaag ttgttggtag tggtg                               35

<210> SEQ ID NO 20
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 20
ggttttgaag ttgtt                                                     15
```

SINGLE-STRANDED OLIGONUCLEOTIDES FOR USE IN THE MEDICAL TREATMENT OF SKIN DISORDERS

This application is a § 371 application of PCT/EP2016/063596, filed Jun. 14, 2016, which in turn claims priority to SE Application 1550814-6, filed Jun. 15, 2015. The entire disclosure of each of the foregoing applications is incorporated by reference herein.

TECHNICAL FIELD

The invention relates to non-CpG single-stranded oligonucleotides (ssONs) for use in the treatment or prophylaxis of disorders of the skin and/or subcutaneous tissue, including pruritus. The said ssONs have a length of at least 25 nucleotides and are stabilized by phosphorothioate internucleotide linkages and/or 2'-O-Methyl modifications.

BACKGROUND ART

Skin is the largest organ of the human body. It serves as a barrier to protect against infection, toxins, microbes, and radiation. Disorders of skin not only compromise these functions, but also cause significantly psychological, social, and occupational problems. A significant portion of the world's population is afflicted with skin problems. Disorders of the skin and/or subcutaneous tissue are coded in ICD-10 (*International Statistical Classification of Diseases and Related Health Problems—10$^{th}$ Revision*), Chapter XII, and includes e.g. atopic dermatitis, psoriasis, rosacea, acne, pityriasis rosea, urticaria, erythema, and pruritus. These disorders account for a large portion of annual healthcare costs, in addition to non-financial costs, such as intractable itching, sleep deprivation, psychiatric co-morbidities time spent in treatment, inconvenience, and associated social stigma. Children with moderate to severe atopic dermatitis (AD) consistently rate their condition as having an impact on quality of life that is comparable to insulin-dependent diabetes [1]. There is a need for treatment of skin disorders. Many of these skin disorders are associated with various degree of inflammation and itch. Inflammation is a tightly regulated process aimed to eliminate intruding pathogens and remove damaged cells. The concerted action of professional phagocytes, such as macrophages, monocytes, neutrophils and certain dendritic cells, is essential to effectively clear the site of dying cells and invading pathogens as well as to restore homeostasis [2]. Dendritic cells (DC) are potent antigen presenting cells with capacity to prime naïve T cells after uptake of antigens but are also involved in keeping tolerance [3]. The functional outcome of DC action is dictated by differential expression of co-stimulatory receptors and inhibitory receptors as well as patterns of cytokine/chemokine secretion. The healthy human skin harbors at least three DC populations: Langerhans cells (LCs) in the epidermis; and interstitial CD1a$^+$ and CD14$^+$ DCs in the dermis [4, 5].

Oligonucleotides are short DNA or RNA molecules, oligomers, that have a wide range of applications. "CpG oligonucleotides" (or CpG-ssON) are short single-stranded synthetic DNA or RNA molecules that contain a cytosine triphosphate nucleotide ("C") followed by a guanine triphosphate nucleotide ("G"). It is known in the art that CpG-containing nucleic acids stimulate the immune system and can be used to treat infectious diseases, allergy, asthma and other disorders. The CpG sequence in ssDNA-ODN ligands has been shown to be indispensable for activation of Toll-like receptor 9 (TLR9), which plays a fundamental role in pathogen recognition and activation of innate immunity. The stimulatory effect of the ligand is lost when the CpG repeats are removed. Consequently, the TLR-mediated immunostimulatory effect has not been shown in single-stranded oligonucleotides lacking CpG motifs ("non-CpG ssON").

It has been shown that stimulation of the immune system with CpG-containing immunostimulatory motifs leads to induction of pro-inflammatory responses accompanied with induction of IL-10 (see examples in U.S. Pat. No. 7,807,803 B2). The anti-inflammatory cytokine IL-10 is well known for its contribution in restoration of homeostasis after cellular injury. Numerous studies in mice have shown that IL-10 is important to limit autoimmune pathologies. IL-10 has been attributed many functions including repression of the major pro-inflammatory cytokines IL-1, IL-6, IL-12 and TNF-α as well as chemokines of both the CC and CXC type [6]. The soluble ILT-6, with anti-inflammatory effects was shown to be up-regulated by IL-10 [7]. Even though the anti-inflammatory effects of IL-10 have been known for a long time and many conditions could be improved by inducing IL-10, there have been difficulties with the attempts to develop therapeutics based on the administration of IL-10. Clinical trials in humans using recombinant IL-10 have shown only marginal success [6].

It has been disclosed (Duffy et al., US2008/0299138 and WO2008/147956; Ranjith-Kumar, C. T. et al. 2008. Molecular and cellular biology 28:4507-4519) that single-stranded DNAs can be used to regulate the inflammatory response through Toll-like receptor 3 (TLR3). It has also been shown by Sköld et al. [8] that single-stranded DNA oligonucleotides (ssONs) inhibit TLR3-mediated responses in human monocyte-derived dendritic cells and in vivo in cynomolgus macaques. TLR3 is a key receptor for recognition of double-stranded RNA and initiation of immune responses against viral infections. However, hyperactive responses can have adverse effects, such as virus-induced asthma. It was shown [8] that human monocyte-derived dendritic cells up-regulate maturation markers and secrete proinflammatory cytokines on treatment with the synthetic TLR3 ligand polyinosine-polycytidylic acid (Poly(I:C)). Poly(I:C) is a synthetic agonist to for example TLR3 and is often used as an adjuvant in vaccines [see e.g. ref. 28]. It is also well known that injection of Poly(I:C) leads to an inflammatory response, for example if administered to the skin [10]. It was shown [8] that TLR3-mediated events were inhibited in cultures with CpG ssON. Poly(I:C) activation of non-hematopoietic cells was also inhibited by CpG ssON. The uptake of Poly(I:C) into cells was reduced in the presence of CpG ssON, preventing TLR3 engagement from occurring. In cynomolgus macaques, the levels of proinflammatory cytokines in nasal secretions were reduced when ssONs were administered via the intranasal route. The ssON sequences used by Sköld et al. were:

5'-GTCGTTTTGTCGTTTTGTCGTTGTTGGTGGTG-GTG-3'
(CpG ssON; SEQ ID NO: 1); and
5'-GAAGTTTTGAGGTTTTGAAGTTGTTGGTGGTG-GTG-3'
(non-CpG ssON; SEQ ID NO: 2).

Today's treatment of inflammatory skin disorders often includes immunosuppressive treatments such as corticosteroids and calcineurin inhibitors [9] and is often accompanied with subsequent infections of the skin due to barrier defects and nonfunctional immune defenses. In addition, prolonged treatment with corticosteroids are associated with well know toxic side effects. The pathogenesis of skin disorders, such as for example atopic dermatitis and psoriasis, were suggested to include dysregulated IL-10 production [10-13].

Many of the skin disorders or pathologies are accompanied by pruritus, a condition involving localized or general itching. A variety of causes for the condition of pruritus are known including external and endogenous causes, localized skin disorders and systemic diseases. Itch can also be produced by a variety of chemical, mechanical, thermal and electrical stimuli [14, 15].

Generally, options for effectively treating these disorders are limited. Currently available treatment modalities for these pathologies include nonspecific topical agents such as emollients and counterirritants, topical and oral drugs such as steroids, local anesthetics and antihistamines, and physical modalities such as ultraviolet phototherapy and thermal stimulation. Some of these treatments are effective in pruritic conditions of a particular etiology, while others may show general but nonspecific benefit. It is known that many corticosteroids can relieve itch and may be effective in treating some skin disorders. However, prolonged use of such corticosteroids is associated with both cutaneous and systemic toxic side effects and their widespread use is limited without medical supervision. Selenium sulfide, sulfur and salicylic acid or tar shampoo have also been employed to treat these skin conditions. In any event, remission of the pathology or pruritus is often slow and frequently incomplete.

Nonspecific topical preparations can act as moisturizing lotions or creams or as oil-based ointments that are occlusive and serve to soften dry skin as well as provide a protective layer. While such preparations may have valuable moisturizing and skin softening properties, they also possess undesirable effects in that they generally impart to the skin an uncomfortable feeling of warmth in addition to a sticky, oily, greasy or waxy feel. More importantly, these materials alone have little effect, if any, on reducing itching.

Hence, today's treatment is not sufficient and there is a need for selective anti-inflammatory compounds that can increase antibacterial defenses and ameliorate itch. There is a need for improved methods for the treatment or prophylaxis of medical conditions such as "disorders of the skin and/or subcutaneous tissue" as defined in ICD-10.

DESCRIPTION OF THE INVENTION

Figure 1A:
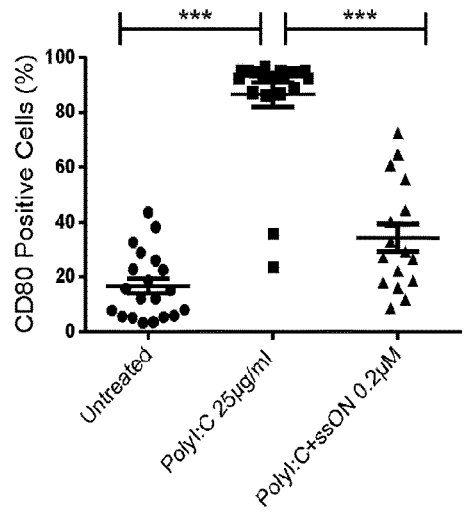
FIG. 1: (A) Immature human DCs exposed to 25 µg/ml Poly(I:C), in the presence of 0.2 µM ssON. Expression of co-stimulatory molecules was measured by flow cytometry. Significant differences were measured by one-way ANOVA (****$P<0.0001$). (B) Immature human DCs exposed to 25 µg/ml Poly(I:C) in the presence of ssON. The inhibition of CD80 and CD86 expression is concentration dependent. Individual data are shown with means±SD. (C) IL-6, IP-10 and IL-1ra was measured in culture supernatants twenty-four hours post-stimulation of DCs (n=6). Significant differences were assessed by non-parametric Kruskal-Wallis test with Dunn's multiple comparisons comparing Poly(I:C) with different concentrations of ssON (*$P<0.05$, $P<0.01$, *$P<0.001$).
Figure 1A:
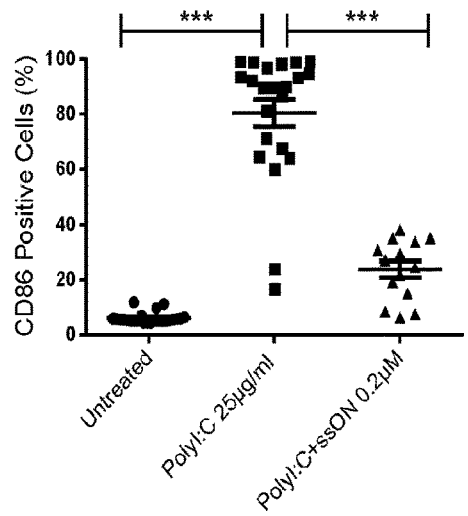
Figure 1A:
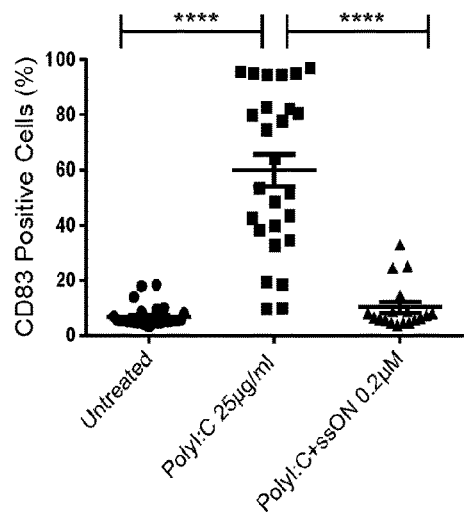

As shown in the Examples below, transcriptional profiling of skin biopsies revealed ssON-dependent dampening of dsRNA-induced pro-inflammatory responses in macaques. The ssON-modulated cytokine pattern was confirmed by protein analyses directly ex vivo from skin biopsies and, surprisingly, revealed induction of IL-10 and inhibition of IL-6 secretion. Transcriptional profiling further revealed unexpected increase in expression of antibacterial peptides after treatment with ssON.

As discussed in the Background Art section, it is known in the art that CpG ssONs are capable of inducing pro-inflammatory responses accompanied with induction of IL-10. It has also been disclosed by Sköld et al. [8] that a non-CpG ssON (SEQ ID NO: 2) could inhibit Poly(I:C)-induced production of pro-inflammatory cytokines. However, according to the invention, it was unexpected that non-CpG ssONs are capable inducing IL-10, as well as antibacterial peptides, without concomitant pro-inflammatory responses.

Consequently, it has surprisingly been shown that ssON (non-CpG) are useful in the treatment and prophylaxis of disorders of the skin and/or subcutaneous tissue, including pruritus.

In a first aspect, this invention provides a single-stranded oligonucleotide (ssON) for use in the treatment or prophylaxis of a disorder of the skin and/or subcutaneous tissue, including pruritus;
wherein:
(a) the length of the said ssON is at least 25 nucleotides;
(b) either (i) at least 90% of the internucleotide linkages in the said ssON are phosphorothioate internucleotide linkages; or (ii) the said ssON comprises at least four (preferably at least five or six) phosphorothioate internucleotide linkages and at least four (preferably at least five or six) 2'-O-methyl modifications; and
(c) the said ssON does not contain any CpG motifs.

The term "disorder of the skin and/or subcutaneous tissue" comprises the medical conditions coded in ICD-10 (International Statistical Classification of Diseases and Related Health Problems, $10^{th}$ revision). Such conditions include e.g. infections of the skin and subcutaneous tissue (e.g. cellulitis); dermatitis and eczema (e.g. atopic dermatitis and/or pruritus); bullous disorders (e.g. pemphigus); papulosquamous disorders (e.g. psoriasis); urticaria and erythema; disorders of skin appendages (e.g. rosacea); or other disorders of the skin and subcutaneous tissue (e.g. lupus erythematosus). These examples are purely illustrative from each category and are not meant to limit the scope of the invention.

In a preferred aspect, the term "disorder of the skin and/or subcutaneous tissue" comprises the medical conditions coded in ICD-10, Chapter XII, L20-L30 "Dermatitis and eczema", such as in particular L20 "Atopic dermatitis" and/or L29 "Pruritus".

In addition, the ssON is useful when an infection is associated with the said disorder of the skin and/or subcutaneous tissue. The infection may be caused by a disrupted skin barrier, the initial treatment, or by changes in the immune system.

As mentioned above, the length of the ssON is at least 25 nucleotides. More preferably, the length is between 25 and 150; between 25 and 70, between 25 and 50, or between 25 and 35 nucleotides.

The terms "phosphorothioate internucleotide linkages" and "PS linkages" refer to internucleotide linkages in which one of the non-bridging oxygens in the DNA phosphate (PO) backbone is replaced by sulfur [16]. Preferably 95%, or more preferably 100%, of the internucleotide linkages in the said ssON to be used according to the invention are phosphorothioate (PS) internucleotide linkages. Consequently, the invention includes the use of ssONs wherein some internucleotide linkages (such as one, two, three or more internucleotide linkages) are PO linkages without sulfur, while the remaining linkages are PS linkages. In cases where the ssON comprises phosphate groups in the 5'-terminal and/or 3-terminal, such phosphate groups may be modified (PS) or unmodified (PO) groups.

The term "2'-O-Methyl modifications" refers to nucleotide modifications wherein a methyl group is added to the 2'-hydroxyl group of the ribose moiety of a nucleoside.

The ssON to be used according to the invention may comprise additional chemical modifications. Chemically modified oligonucleotides are known in the art and disclosed in e.g. Jäarver, P. et al. 2014. *Nucleic acid therapeutics* 24:37-47; and Deleavey, G. F. & Damha, M. J. 2012. *Chemistry & Biology* 19:937-954. Possible chemical modifications include e.g. LNA (Locked Nucleic Acid), wherein the ribose moiety is modified with an extra bridge connecting the 2' oxygen and 4' carbon. Further, the ssON could comprise a mix of ribose and deoxyribose as the five-carbon sugar. In addition, one or more nucleobases in the ssON could be modified. Oligonucleotide base modifications include methylation of cytosine to form 5-methylcytosine, and methylation of adenosine to form N6-methyladenosine.

The term "CpG motifs" will be understood to refer to immunostimulatory CpG oligonucleotides, i.e. short single-stranded synthetic nucleic acid molecules that contain a cytosine triphosphate deoxynucleotide ("C") followed by a guanine triphosphate deoxynucleotide ("G"). The "p" refers to the phosphodiester or phosphorothioate link between consecutive nucleotides. CpG motifs are considered pathogen-associated molecular patterns (PAMPs) due to their abundance in microbial genomes but their rarity in vertebrate genomes. The CpG PAMP is recognized by the pattern recognition receptor (PRR) Toll-Like Receptor 9 (TLR9), which is constitutively expressed primarily in B cells and plasmacytoid dendritic cells (pDCs) in humans and other higher primates. Consequently, the invention does not include the use of ssONs comprising CpG motifs capable of stimulating a TLR9 response.

Preferably, the ssON to be used according to the invention has a "sequence independent" mode of action, does not have antisense activity and is not complementary to a gene. More specifically, not more than 16 consecutive nucleotides in the said ssON are complementary with any human mRNA sequence. Consequently, the ssON is essentially "non-complementary" with any human mRNA sequence. The term "non-complementary" will be understood to refer to nucleic acid sequences that are not capable of precise pairing (of purine or pyrimidine bases between the two strands of nucleic acids sequences) under moderate or stringent hybridization conditions (i.e. 5-10° C. below $T_m$). In particular, the ssON is non-complementary to nucleotide sequences coding for receptor proteins, e.g. Toll-like receptors, such as TLR3 or TLR9, or any other protein which recognize DAMPs (Damage-associated molecular pattern) or PAMPs (Pathogen-associated molecular pattern molecules). It will thus be understood that the ssONs to be used according to the invention are not "antisense" molecules that are complementary to a messenger RNA (mRNA) strand transcribed within a cell.

A person having ordinary skill in the art will be able to identify oligonucleotide sequences which are "non-complementary" as defined according to the present invention. For instance, the skilled person could use well-known tools such as the BLAST algorithm as implemented online by the US National Center for Biotechnology Information. See e.g. Madden, T. 2013. The BLAST Sequence Analysis Tool. The NCBI Handbook [Internet], $2^{nd}$ edition. (www.ncbi.nlm.nih.gov/books/NBK153387)

Preferably, the said ssON is not self-complementary. The term "not self-complementary" will be understood to mean that the ssON does not have any self-complementary sequences that would allow two ssONs to dimerize, or that would allow parts of the oligonucleotide to fold and pair with itself to form stem loops. It is well-known that stem loop (also referred to as "hair-pin" loop) base pairing can occur in single-stranded DNA or RNA. It occurs when two regions of the same strand, usually complementary when read in opposite directions, base-pair to form a double helix that ends in an unpaired loop.

A person having ordinary skill in the art will be able to identify self-complementary sequences by comparing parts of the ssON sequence and detecting whether Watson-Crick base pairing (CG and AT/AU) could occur. Alternatively, a software tool such as Oligo Calc: Oligonucleotide Properties Calculator (www.basic.northwestern.edu/biotools/oligocalc.html) could be used to detect self-complementary sequences. Models for self-dimerization and hairpin formation in oligonucleotides are known in the art and are described in e.g. Hilbers, C. W. 1987. *Anal Chem* 327:70; Serra, M. J. 1993. *Nucleic Acids Res* 21:3845-3849; and Vallone, P. M. 1999. *Biopolymers.* 50:425-442. As a general rule, at least 5 base pairs would be required for self-dimerization, and at least 4 base pairs would be required for hair-pin formation. Consequently, preferably the ssON as defined above does not comprise more than 3 consecutive nucleotides that could form base pairs with another sequence of 3 consecutive nucleotides at the same ssON molecule.

Preferably, the said ssON is a single-stranded oligodeoxynucleotide (ssODN). However, the invention also provides the use of ssONs that are stabilized single-stranded RNA (ribonucleic acid) molecules. As will be understood by the skilled person, when the ssON is an oligodeoxynucleotide, the monosaccharides in the ssON are 2'-deoxyribose. However, in the present context the term "ssODN" also includes oligonucleotides comprising one or more modified monosaccharides such as 2'-O-methylribose.

In preferred aspects of the invention, the ssON comprises the sequence shown as SEQ ID NO: 2, 12, 13, 14, 15, 16, or 19 in the Sequence Listing. More preferably, the ssON has (consists of) the sequence shown as SEQ ID NO: 2, 12, 13, 14, 15, 16, or 19. In a further preferred aspect of the invention, at least 30% of the nucleobases in the ssON are chosen from A (Adenine) and T (Thymine) and U (Uracil). Preferably, at least 35%, 40%, 45%, 50%, 55%, or 60% of the nucleobases in the ssON are chosen from A, T and U. When the ssON is an oligodeoxynucleotide (ssODN), containing deoxyribose as its pentose component, the nucleobases are normally chosen from A and T. When the ssON is a ribonucleotide containing ribose, the nucleobases are normally chosen from A and U. However, the ssONs according to the invention could include synthetic variants which may differ from naturally occurring oligonucleotides. For instance, the ssON could comprise a deoxyuridine moiety (i.e. uracil bound to deoxyribose). The ssON could also comprise nucleobase analogues, which are well known in the art and include e.g. xanthine, hypoxanthine, 7-methylguanine, 5-methylcytosine, and 5-hydroxymethyl-cytosine.

The invention provides ssONs as disclosed above for use in the treatment or prophylaxis of medical conditions in mammals, in particular humans, wherein the route of administration is selected from parenteral, intramuscular, subcutaneous, epidermal, intradermal intraperitoneal, intravenous, mucosal delivery, oral, sublingual, dermal, transdermal, topical, inhalation, intranasal, aerosol, intraocular, intratracheal, intrarectal, vaginal, gene gun, dermal patch, eye drop or mouthwash.

In one aspect, the said ssON can be locally administered to a tissue in an amount of from about 70 µg to about 5 mg/dose, preferably from about 70 µg to about 700 µg/dose. The range 70-700 µg corresponds to about 6-60 nmol ssON and is preferably applied per $cm^2$ of skin or mucosa. Alternatively, the said ssON can be systemically administered in an amount from 10 µg/kg to 10 mg/kg body weight; preferably from about 10 µg/kg to about 1 mg/kg; more preferably from about 10 µg/kg to about 100 µg/kg.

It will be understood that the ssON to be used according to the invention can be administered in combination with other agents, e.g. anti-inflammatory and/or anti-pruritic agents such as calcineurin inhibitors, corticosteroids, anti-IL31, PDE-4 inhibitor, IL-4R antibody, anti-IL13, anti-IL22, anti-IL12/23, SB011 (cleaves GATA-3 mRNA) removal/inhibition of IgE, DP2 antagonist, neurokinin-1 receptor antagonist, topical non-steroidal anti-inflammatory reagents such as LE032731 and GSK2894512, Clonidine, Naltrexone, 5-HT2B receptor antagonist, and/or anti-histamine treatments.

In another aspect, the invention provides a method for the treatment or prophylaxis of a disorder of the skin and/or subcutaneous tissue and pruritus; said method comprising administering to a mammal, such as a human, in need of such treatment or prophylaxis an effective amount of an ssON as defined above.

In another aspect, the invention provides a pharmaceutical composition comprising an ssON as defined above, together with a pharmaceutically acceptable carrier. In a preferred aspect, the pharmaceutical composition is adapted for use in the treatment or prophylaxis of a disorder of the skin and/or subcutaneous tissue, including pruritus.

In a further aspect, the invention provides a single-stranded oligonucleotide (ssON), wherein the said ssON comprises the nucleotide sequence shown as SEQ ID NO: 15 or 16; provided that the ssON does not have the sequence shown as SEQ ID NO: 2.

Preferably, the said ssON comprising the nucleotide sequence shown as SEQ ID NO: 15 or 16 has at least one, more preferably two, three, four or five, of the following features:
 (a) the length of the said ssON is between 25 and 70 nucleotides, more preferably between 25 and 35 nucleotides;
 (b) either (i) at least 90% (preferably 95% or 100%) of the internucleotide linkages in the said ssON are phosphorothioate internucleotide linkages; or (ii) the said ssON comprises at least four (preferably at least five or six) phosphorothioate internucleotide linkages and at least four (preferably at least five or six) 2'-O-methyl modifications; and
 (c) the said ssON does not contain any CpG motifs;
 (d) not more than 16 consecutive nucleotides in the said ssON are complementary with any human mRNA sequence;
 (e) the said ssON is not self-complementary.

Preferably, the said ssON comprises a nucleotide sequence shown as SEQ ID NO: 12, 13, 14, or 19. More preferably, the said ssON has a nucleotide sequence shown as SEQ ID NO: 12, 13, 14, 15, 16, or 19.

EXPERIMENTAL METHODS

Synthesis of Oligonucleotides

Synthetic, endotoxin-free, oligonucleotides were synthesized according to methods known in the art, as disclosed in e.g. *Artificial DNA: Methods and Applications* (Khudyakov, Y. E. & Howard A. Fields, H. A., Eds.) CRC Press, 2002 (ISBN 9780849314261). The synthesized oligonucleotides do not carry any phosphate groups on neither the 5'-terminus, nor the 3'-terminus.

Reagents

High molecular weight Poly(I:C) (InvivoGen) was used at 25 µg/mL unless otherwise stated. Lipopolysaccharide (LPS; 100 ng/mL; Sigma-Aldrich) was used as a positive control for DC maturation.

Human In Vitro Derived DCs

Monocytes were negatively selected from buffy coats using the RosetteSep Monocyte Enrichment Kit™ (1 mL/10 mL buffy coat; StemCell Technologies) and differentiated into DC, as described previously [8] at a density of $5 \times 10^5$ cells/mL in RPMI 1640 completed with 10% FCS, 1 mM sodium pyruvate, 10 mM HEPES, 2 mM L-glutamine, and 1% streptomycin and penicillin (all from Invitrogen Life Technologies), with GM-CSF (250 ng/mL; PeproTech) and IL-4 (6.5 ng/mL; R&D Systems) for 6 or 7 days. The cells were phenotyped with Abs against CD14, CD1a (both from DakoCytomation), CD3, and CD19 (both from BD Biosciences). Maturation was assessed 48 h post-stimulation using Abs targeting CD1a (DakoCytomation), CD80, and CD86 (both from BD Biosciences). Sample data were acquired on a FACSCalibur™ or Fortessa™ (BD Biosciences); the analysis was performed with FlowJo™ software (TreeStar).

Animals and Injections

Adult cynomolgus macaques (*Macaca fascicularis*), imported from Mauritius, were housed in CEA facilities (accreditation no. B 92-032-02) and handled in accordance with European guidelines for NHP care (EU Directive N 63/2010). The study was approved by the regional committee for animal care and use (Comité Régional d'Ethique Ile de France Sud). Animals, tested and found seronegative for several pathogens (SIV, HBV, filovirus, measles and herpes B viruses), were handled under sedation with an intramuscular (i.m.) injection of 10 mg/kg ketamine chlorhydrate (Imalgen) and 0.5 mg/kg of acepromazine (Vtranquil™, CEVA SANTE ANIMALE). Intradermal (i.d.) injections, via a 29 gauge needle, were done in the upper left and right back flank with 170 µg of Poly(I:C) (InvivoGen) alone or with 170 µg of ssON (DNA Technology A/S) in 100 µL of PBS, or PBS alone. Alternatively a dose escalation with ssON was performed as indicated in figure legends.

Macaque Tissue Collection and Flow Cytometry

Cells were extracted from fresh skin biopsies (8 mm in diameter) collected from anesthetized animals 24 h after injection. Previous studies in human subjects revealed peak responses at 24 hours in the majority of individuals after inoculation of Poly(I:C) [17]. The kinetic proteome analyses of Poly(I:C) stimulated human monocyte derived DCs presented here showed peak responses 8-24 hours post-stimulation with no earlier responses detected. Later responses measured 48 hours post-stimulation of human DCs in vitro shows diminished cytokine production. Altogether, this was the rationale for choosing the 24-hour time point for biopsy collections and transcriptional analyses in the non-human primates.

The subcutaneous fat was removed and the biopsies collected for cell suspension analyses were incubated in PBS containing 4 mg/ml grade II dispase (Roche Diagnostic) and 100 µg/ml of Penicillin/Streptomycin/Neomycin (Life Technologies) over night at 4° C. and then for one hour at 37° C. with 5% $CO_2$. Epidermis and dermis layers were separated, the dermis were cut into small pieces, and the layers were incubated for 20 or 40 min, respectively, at 37° C. with shaking in RPMI-1640 (Life Technologies) containing 2 mg/ml of collagenase D, 0.02 mg/mL DNAse I (both from Roche Diagnostic), 10 mM HEPES (Life Technologies), 5% fetal calf serum (Lonza) and 100 µg/ml of Penicillin/Streptomycin/Neomycin. Cell suspensions were then filtered through a 70 µm pore size filter. The residues on the filter were discarded for the epidermis while the dermal residues were mechanically dissociated through GentleMACDS™ dissociator (Miltenyi) and then re-filtered. Filtrates were centrifuged at 1800 rpm for 10 min before incubation with LIVE/DEAD Fixable Blue Dead Cell Stain Kit™ (Life Technologies), according to the manufacturer's instructions. All the isolated epidermal and dermal cells were stained with a mix of monoclonal antibodies (mAb) and acquired on a Fortessa™ flow cytometer (BD Biosciences). Fluorochrome-free Ab was detected with a secondary Ab coupled to an Alexa Fluor 700™ fluorochrome with the Zenon® Kit (InvitroGen) according to manufacturer's instructions. Data were analyzed with FlowJo™ software (Tree Star, version 9.6.4).

Cytokine Secretion Assays

To evaluate cytokine and chemokine production from macaque skin biopsies directly ex vivo, aliquots of filtered-dermis supernatants were collected and measured with the MILLIPLEX MAP NHP Cytokine Magnetic Bead Panel™ (Millipore) on a Bio-Plex™ device (Bio-Rad), according to manufacturer's instructions. Human DC culture supernatants collected 24 hours after in vitro stimulation were measured with custom made multiplex analyses on a MAGPIX™ device (Bio-Rad).

Microarray Analysis

Whole skin RNA were extracted from macaque skin biopsies, stored at least 24 h at 4° C. in RNA Later, using Tissue Ruptor® followed by RNeasy Plus Universal Kit™ (QIAgen), according to manufacturer's instructions. Blood was collected from the macaques in Tempus™ Blood RNA Tube (Applied Biosystems) for whole-blood RNA isolation at baseline (day 0) and 24 h after administration of Poly(I:C) or Poly(I:C)/ssON. In brief, RNA was extracted using Tempus™ Spin RNA Isolation kit (Applied Biosystems) according to the manufacturer's protocol. Total RNA was quality checked on Agilent 2100 Bioanalyzer™. RNA quantity was measured using NanoDrop ND-1000™ Spectrophotometer. Cyanine-3 (Cy3) labeled cRNA was prepared from 200 ng Total RNA using the Quick Amp Labeling Kit™ (Agilent) according to the manufacturer's instructions, followed by RNeasy column purification™ (QIAGEN, Valencia, Calif.). Dye incorporation and cRNA yield were checked with the NanoDrop ND1000™ Spectrophotometer. 1.65 µg of Cy3-labelled cRNA was fragmented at 60° C. for 30 minutes in a reaction volume of 55 µL containing 1× Agilent fragmentation buffer and 2× Agilent blocking agent following the manufacturer's instructions. On completion of the fragmentation reaction, 55 µL of 2× Agilent hybridization buffer was added to the fragmentation mixture and hybridized to Agilent Rhesus Macaque Gene Expression Microarrays v2 for 17 h at 65° C. in a rotating Agilent hybridization oven. After hybridization, microarrays were washed 1 min at room temperature with GE Wash Buffer 1 (Agilent) and 1 min with 37° C. GE Wash buffer 2 (Agilent). Slides were scanned immediately after washing on the Agilent DNA Microarray Scanner™ (G2505C) using one color scan setting for 4×44K array slides (Scan Area 61×21.6 mm, Scan resolution 5 µm, Dye channel is set to Green, PMT is set to 100%). The scanned images were analyzed with Feature Extraction Software 10.7.3.1™ (Agilent) using default parameters to obtain background subtracted and spatially detrended Processed Signal intensities. The signals were background correction by the RMA method and quintile-normalized. Prior to generating heat maps, $\log_2$ transformation was applied on the gene expression data.

For both protein and RNA-data, matching of regulated molecule subsets was performed against known interferon-related genes [17] and to 84 key genes related to NF-κB-mediated signal transduction (The Human NF-κB Signaling Pathway $RT^2$ Profiler PCR Array, Qiagen.com).

Pathway Analysis

Ingenuity Pathway Analysis™ software (Ingenuity Systems) was used to identify canonical signaling pathways regulated by Poly(I:C) alone or in combination with ssON. For calculation of significance of enrichment (Fisher's exact test performed within the software) reference dataset used was Agilent Rhesus Macaque Gene Expression Microarrays v2.

Statistical Analysis

Statistical analyses were performed with Prism 5.0™ (Graph-Pad Software Inc.) using nonparametric Kruskal-Wallis unpaired test followed by Dunn's post-test (*$P<0.05$, $P<0.01$ and *$P<0.001$) or one-way Anova. When indicated different treatment groups were compared using nonparametric Mann-Whitney unpaired tests.

EXAMPLES

Example 1: SsON Inhibits DC Maturation and Pro-Inflammatory Cytokine Responses In Vitro It was shown that immature DC up-regulated the co-stimulatory molecules CD80 and CD86, as well as the maturation marker CD83, after stimulation with the dsRNA mimic Poly(I:C) (FIG. 1A). The dsRNA-induced maturation was significantly inhibited in the presence of the 35-mer ssON designated "nonCpG 35 PS" (Table II) ($p<0.0001$) (FIG. 1A). The ssON "nonCpG 35 PS" contained phosphorothioate (PS) modifications, which have been used to increase half-life of ssONs [18].

Figure 1B:
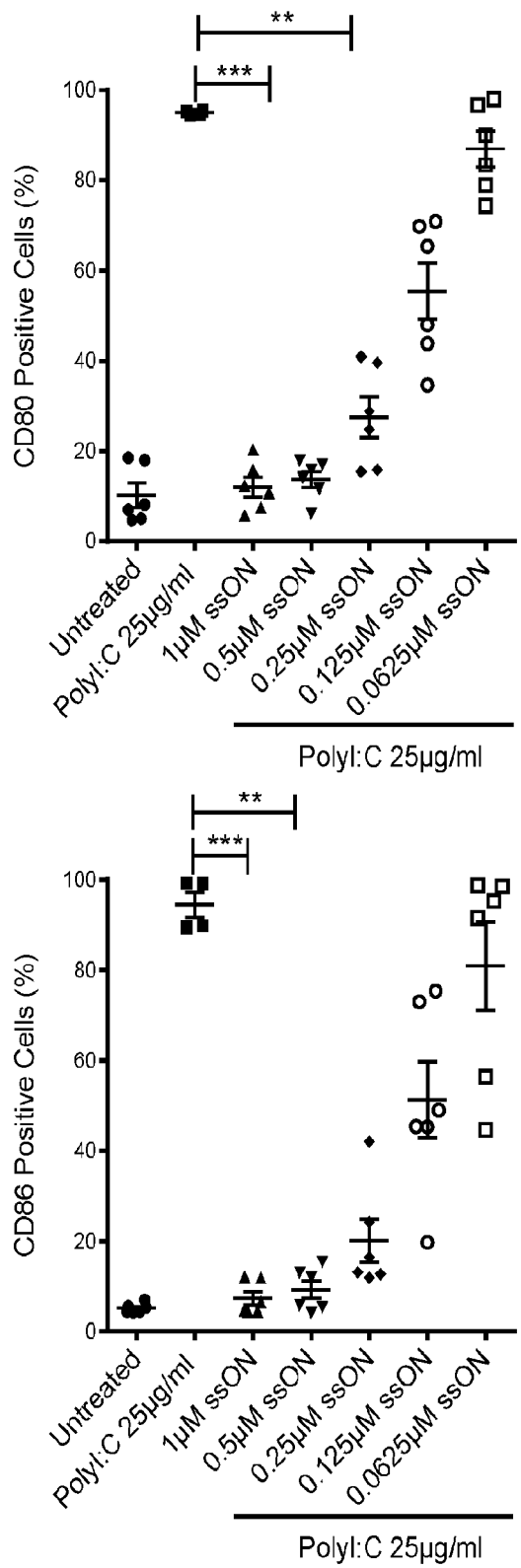
Figure 1C:
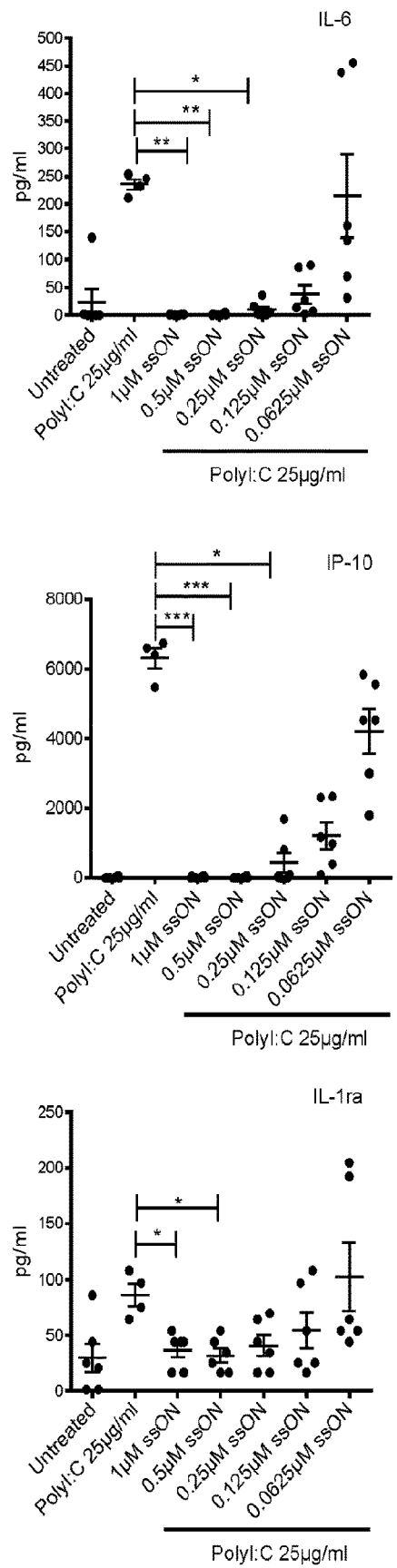

SsON was titrated on human monocyte derived DCs activated with Poly(I:C) (FIG. 1B). Flow cytometry was used to measure expression of the co-stimulatory molecules CD80 and CD86. Bio-Plex™ analysis was used to quantify cytokines released in the supernatants. Poly(I:C) induced significant DC maturation, as defined by up-regulation of the co-stimulatory molecules CD80 and CD86 (FIG. 1B) and pro-inflammatory cytokine release (IL-6, IP-10 and IL1ra) (FIG. 1C). There was a dose-dependent inhibition of dsRNA-mediated DC maturation and pro-inflammatory cytokine release by the ssON with an $IC_{50}$ of approximately 0.2 µM.

Example 2: Intradermal Injection of ssON Modulates Local Cellular Infiltration in Non-Human Primates To assess local inflammation induced after intradermal injection of Poly(I:C) in cynomolgus macaques, skin biopsies were collected from the injection sites twenty-four hours after injection. Multicolor flow cytometry was used to phenotype cells isolated from epidermal and dermal layers.

Figure 2A:
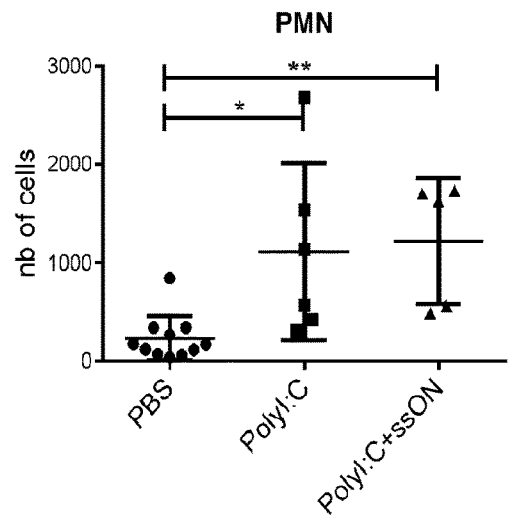
FIG. 2: Intradermal injection of dsRNA (Poly(I:C)) induces local inflammation in non-human primates as expected. Number of immune cell populations identified by flow cytometry in (A) epidermal and (B, C) dermal layers. Cells were collected from biopsies, twenty-four hours after injection with either PBS (n=12), Poly(I:C) (n=6) or Poly (I:C)/ssON (n=6). One outlier animal was excluded from results depicted from epidermal cells. Data are shown with means±SEM. Significant differences were assessed by non-parametric Kruskal-Wallis test and Dunn's post-test (*$P<0.05$,$P<0.01$ and *$P<0.001$). Different treatment groups were compared using nonparametric Mann-Whitney unpaired test, as indicated (dashed arrows).
Figure 2A:
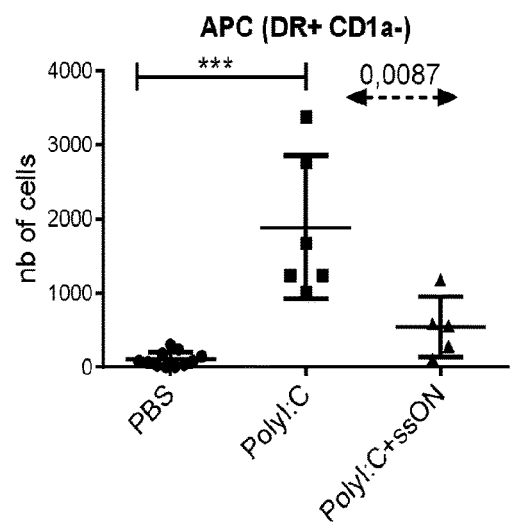
Figure 2A:
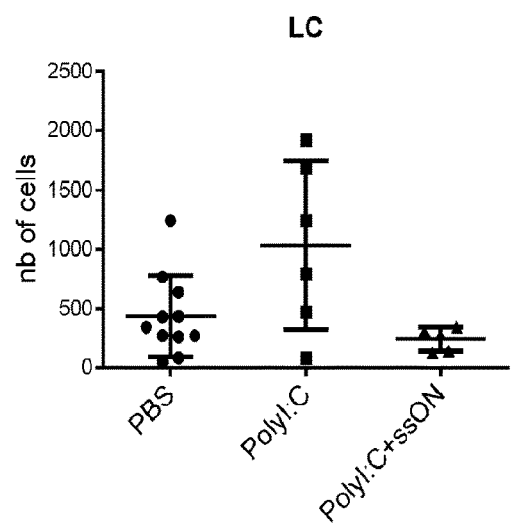

In the epidermis, three main leukocyte populations were identified. Langerhans Cells (LC) expressed CD45 and high levels of HLA-DR as well as CD1a. $CD45^+$ cells expressing HLA-DR but not CD1a were denoted antigen-presenting cells (APC). Polymorphonuclear cells (PMN) including neutrophils, eosinophils and basophils, were defined by their $CD45^+$ $CD66^+$ phenotype [19]. PMNs were mostly absent at the PBS control site. However, a significant influx of PMN and APC was detected after Poly(I:C) injection, and there was a clear trend of increased LC numbers (FIG. 2A). There was a significant infiltration of PMN after simultaneous injection of ssON and Poly(I:C) ($p<0.005$) (FIG. 2A, upper panel). However, there were significantly fewer APC present in the epidermis after Poly(I:C)/ssON treatment compared with Poly(I:C) alone (FIG. 2A, middle panel) and a similar trend was observed for the LC population (FIG. 2A, lower panel). The used ssON was "nonCpG 35 PS" (Table II).

Figure 2B:
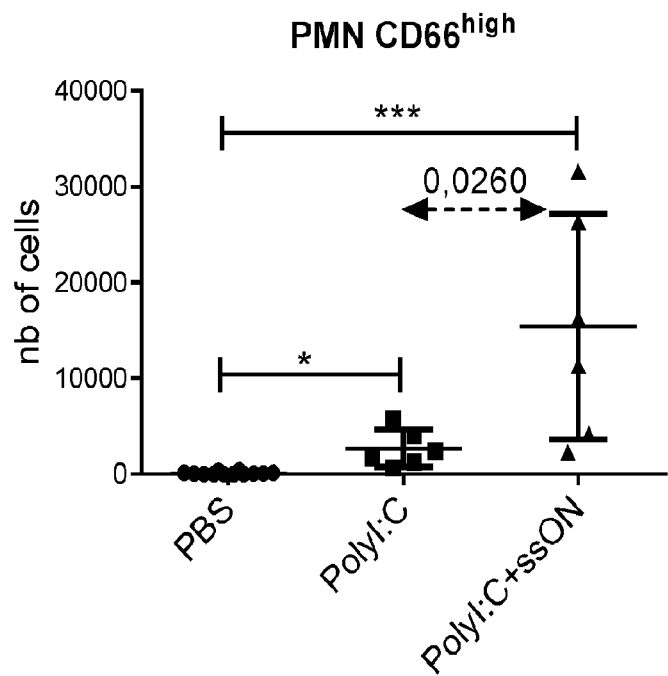
Figure 2B:
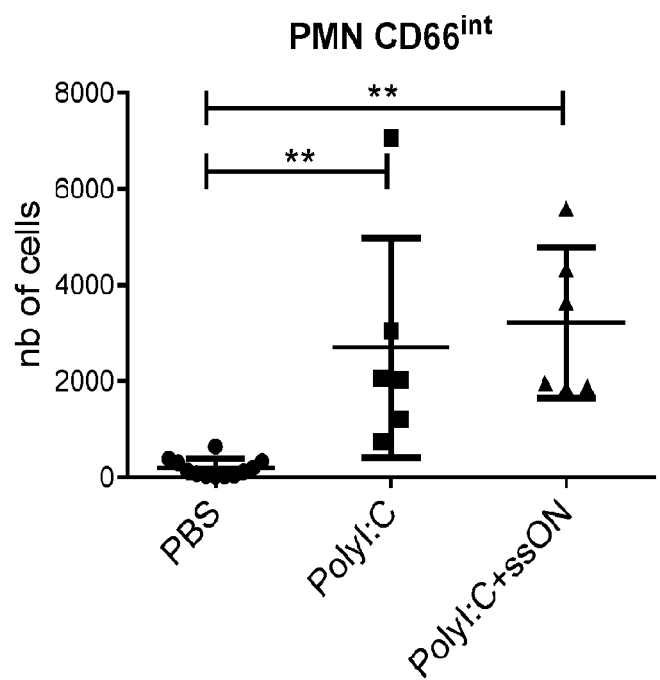

In the dermis, additional immune cell populations were identified through their differential expression of four supplementary surface markers (CD11c, CD163, CD123, CD14) (Zaba, L. C. et al. 2007. *The Journal of clinical investigation* 117:2517-2525; Klechevsky, E. et al. 2008. *Immunity* 29:497-510). As detected in the epidermis, Poly(I:C) injection provoked a significant recruitment of PMN which was strengthened in the presence of ssON (FIG. 2B). Two different PMN populations were detected, one expressing high levels of CD66 (FIG. 2B, top panel) and the other showed an intermediate expression level of CD66 (FIG. 2B, lower panel).

Figure 2C:
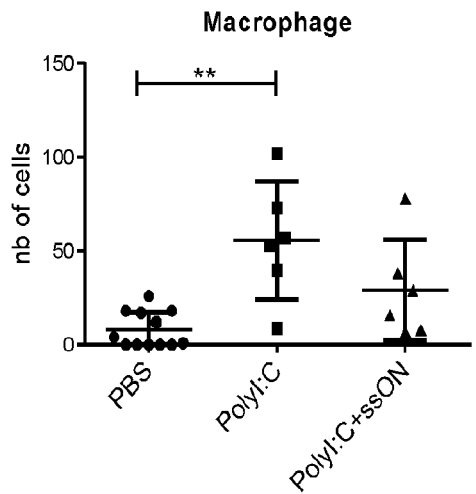
Figure 2C:
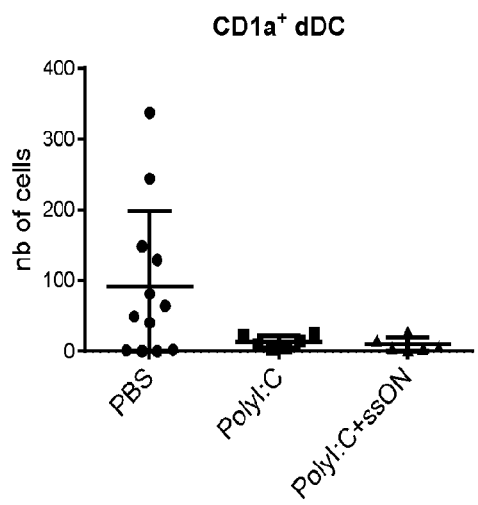
Figure 2C:
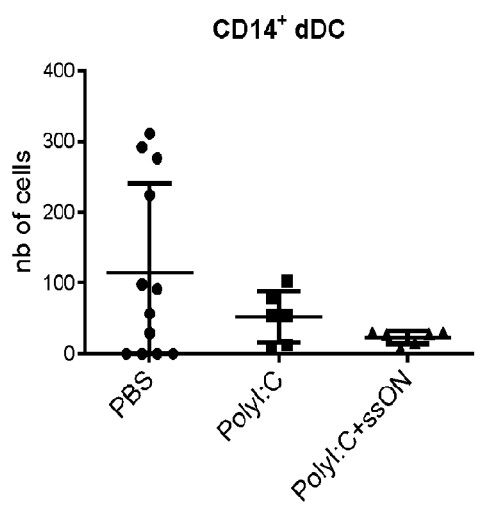

Macrophages, as defined by expression of $CD45^+$ $CD11c^{low}$ $HLA-DR^+$ $CD14^+$, were almost absent in control biopsies (PBS injection), and accumulated when Poly(I:C) was administered alone, while addition of ssON resulted in lower influx. Finally, $CD1a^+$ and $CD14^+$ dermal DC, both subsets defined by additional expression of $CD45^+$ $CD11^+$ $HLA-DR^+$, were recovered from control biopsies and seemed to disappear after intradermal injections with either Poly(I:C) or Poly(I:C)/ssON (FIG. 2C). Importantly, the quantity of cells collected was dependent on the treatment because very few if any $CD45^+$ $CD66^+$ PMNs were found at the PBS control site.

In summary, PMNs are considered to be a typical inflammatory cell population. Hence, the phenotype of the infiltrating PMNs after ssON administration would suggest recruitment of "inflammatory cells" to the site of injection. It was consequently surprising that ssONs, without any CpG motifs, are null to the immune system or only possess "anti-inflammatory" signatures.

Example 3: Transcriptional Profiling

To assess the global innate response to Poly(I:C) in the presence or absence of ssON, whole transcriptional profiling was performed on whole blood samples and skin biopsies obtained from macaques as described under "Experimental Methods". The majority of top 50 responsive genes (FC range 3.5-22; $p<0.05$) detected in blood twenty-four hours after intradermal injection with Poly(I:C) were either IFN-regulated genes or associated with NF-κB activation confirming response patterns previously reported in blood from human subjects [17]. No significant differential expression was detected in blood in the group that received Poly(I:C) and ssON ("nonCpG 35 PS"; Table II) relative to baseline (15% FDR).

The expression profiles of the skin biopsies displayed an even more robust and high induction of innate immune response genes also reflecting influx of cells. Many of the top 50 induced genes in the skin were, similarly, IFN-regulated genes with a FC range of 29-1870 at 5% FDR after Poly(I:C) injection and a FC range of 28-929 at 5% FDR after Poly(I:C)/ssON co-administration. To get more insight as to which genes were differentially down-regulated in the skin by the addition of ssON, the fold change between the treatment group receiving intradermal injection with Poly (I:C) in combination with ssON and the group receiving only Poly(I:C) was calculated. The top down-regulated genes (negative FC>2 p<0.05) after addition of ssON (Table I) include chemokines and genes implicated in inflammatory conditions.

To detect molecular signatures within a set of genes which are co-expressed or co-regulated, canonical pathway analysis was performed using the Ingenuity Pathway Analysis™ software. Several pathways for innate immunity such as "Communication between innate and adaptive immune cells", "Crosstalk between dendritic cells and natural killer cells" and "TREM1 Signaling" were engaged and includes induction of pro-inflammatory cytokines and interferon signaling, consistent with the molecular signatures discovered in the proteomic profiling of dendritic cells. In addition, Poly(I:C) stimulated DC maturation in concordance with the flow cytometry data obtained.

Figure 3A:
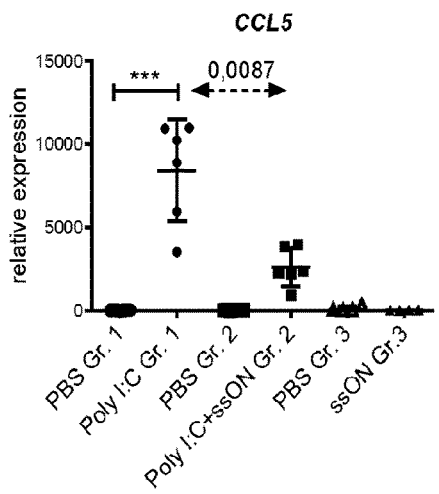
FIG. 3: The ssON treatment dampens expression of several chemokines (A, B) induced by dsRNA in non-human primates and up-regulates inhibitory receptors (C) and antibacterial molecules (D). Relative mRNA expression values obtained from the microarray analyses of individual macaque skin biopsies collected twenty-four hours post-stimulation are shown with means±SEM. Significant differences were assessed by non-parametric Kruskal-Wallis test and Dunn's post-test (*$P<0.05$, $P<0.01$ and*$P<0.001$). Different treatment groups were compared using nonparametric Mann-Whitney unpaired test, as indicated (dashed arrows).
Figure 3A:
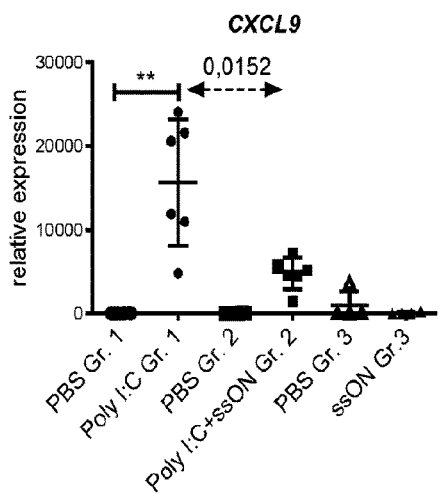
Figure 3A:
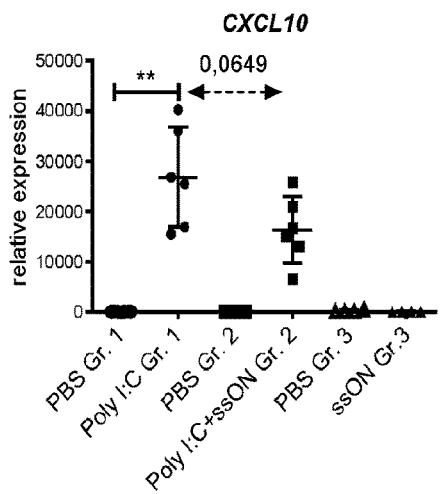
Figure 3B:
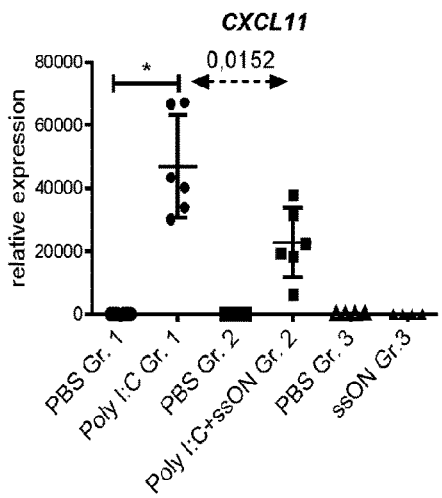
Figure 3B:
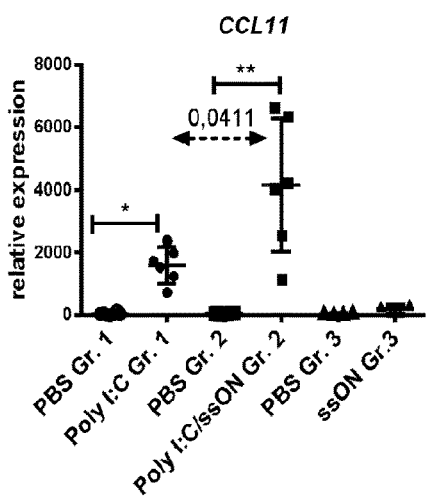
Figure 3B:
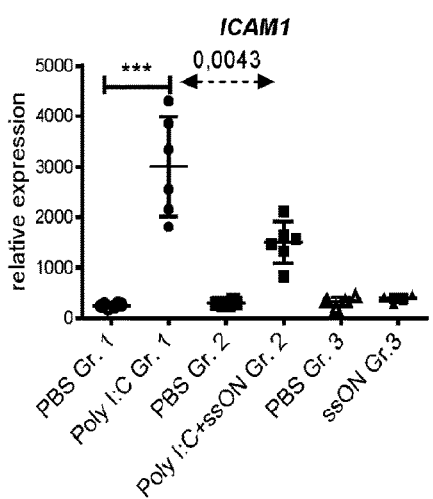

The top 50 regulated genes after stimulation with either Poly(I:C) or Poly(I:C)/ssON were listed in heat maps. From inspecting these lists, it became apparent that several chemokines were differentially induced after addition of ssON. Poly(I:C) treatment resulted in significant induction of Ccl5, Cxcl9, Cxcl10 (FIG. 3A), as well as Cxcl11 and Ccl11 (FIG. 3B), in agreement with recruitment of cells to the skin (cf. Example 2). The induction of chemokines was modulated by ssON, showing reduced expression of Ccl5, Cxcl9, Cxcl10, Cxcl11 and a further increase of Ccl11 expression [20], consistent with increased influx of PMNs, in animals receiving combined Poly(I:C)/ssON treatment. Furthermore, injection of dsRNA resulted in significant increase of Icam1 expression, while the simultaneous treatment with Poly(I:C)/ssON, led to lower expression of Icam1 (FIG. 3B).

Figure 3C:
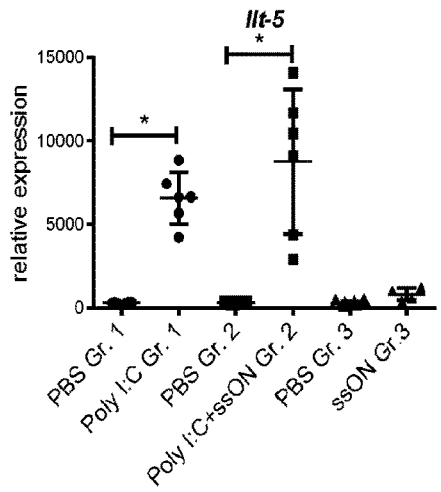
Figure 3C:
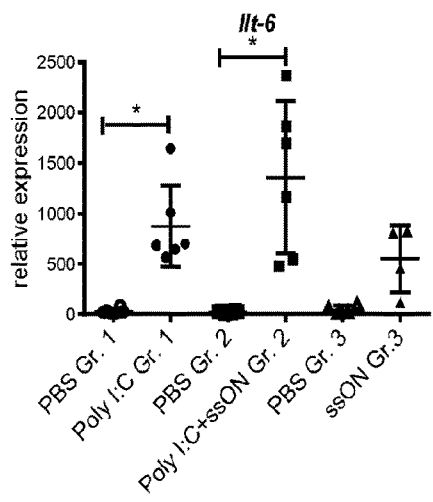
Figure 3C:
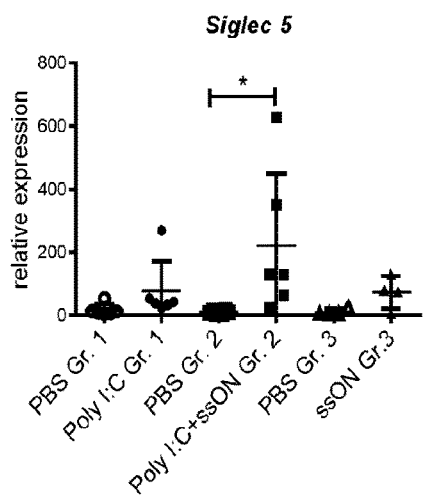

Another set of genes among the top regulated genes were the immunoglobulin-like transcript receptors (ILT) [21, 22]. The ILTs are highly expressed on monocytes, macrophages and dendritic cells where they can inhibit TLR-mediated responses and modulate adaptive responses [23-25]. ILT6 (also named LILRA3) was proposed to be a soluble anti-inflammatory protein that is up-regulated by IL-10 and down-regulated by TNF-α. Increased expression of Ilt5 and Ilt6 after intradermal injection of Poly(I:C), as well as a clear trend of an even higher expression after Poly(I:C)/ssON treatment, were shown (FIG. 3C). A similar up-regulation following ssON treatment was detected for Siglec 5, which is another inhibitory receptor on phagocytes [26].

Figure 3D:
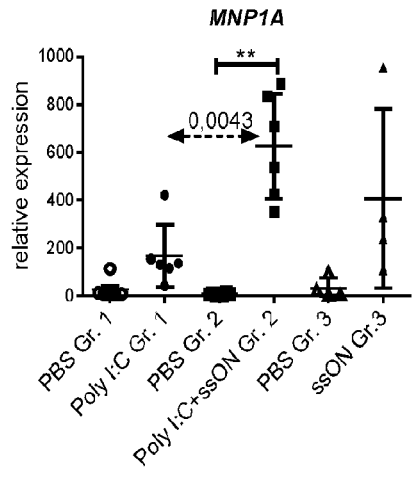
Figure 3D:
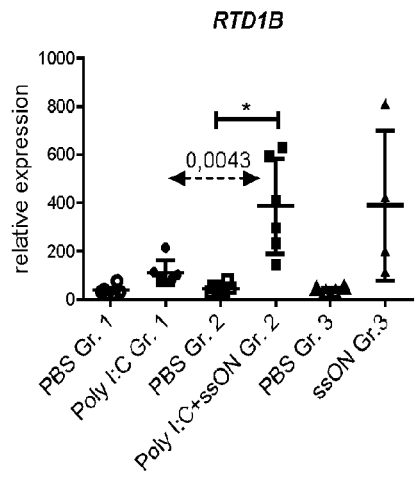
Figure 3D:
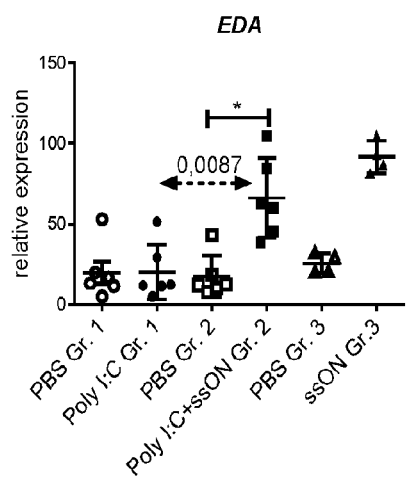

It was further observed that several antimicrobial genes showed relative higher expression after combined Poly(I:C) and ssON treatment as compared with Poly(I:C) alone, such as alpha-defensin 1A (MNP1A) and demidefensin (RTDB1) (29). Also ectodysplasin A (EDA), belonging to the TNF family (30) showed relative higher expression after combined Poly(I:C) and ssON treatment, as compared with Poly(I:C) alone (FIG. 3D).

In summary, the transcriptional analyses revealed a complex unexpected immunomodulatory signature. The addition of ssON resulted in selective inhibition of pro-inflammatory responses such as IL-6, IFN-gamma, CCL5, CXCL9, CXCL10 (also known as IP-10) and CXCL11. However, ssON treatment in the skin induced CCL11 and antibacterial peptides.

Figure 4A:
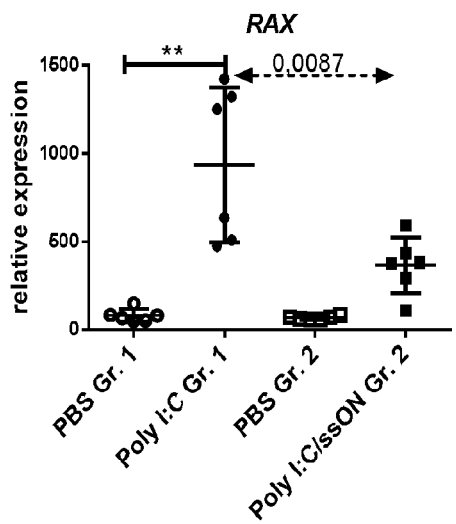
FIG. 4: Relative mRNA expression values obtained from the microarray analyses of macaque skin biopsies for RAX, LRG1 and LCN2 (A) as well as IL-6, IFN-γ and IL-12p40 (B) are shown with means±SEM. Biopsies were collected twenty-four hours after intradermal injections of PBS, Poly (I:C), Poly(I:C)/ssON or ssON. Significant differences were assessed by nonparametric Kruskal-Wallis test and Dunn's post-test (*$P<0.05$, $P<0.01$ and *$P<0.001$). Different treatment groups were compared using nonparametric Mann-Whitney unpaired test, as indicated (dashed arrows).
Figure 4A:
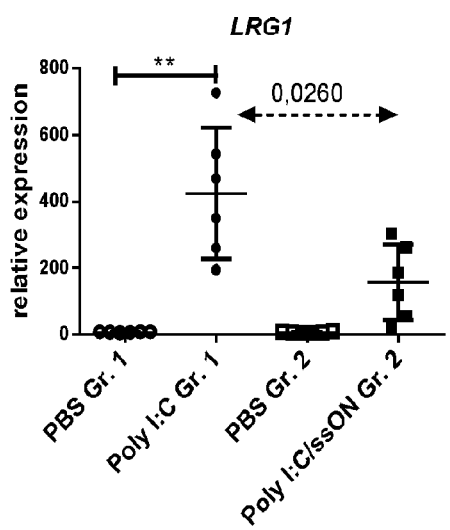
Figure 4A:
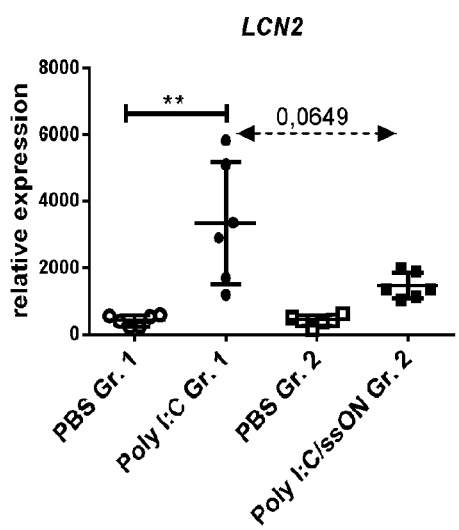
Figure 4B:
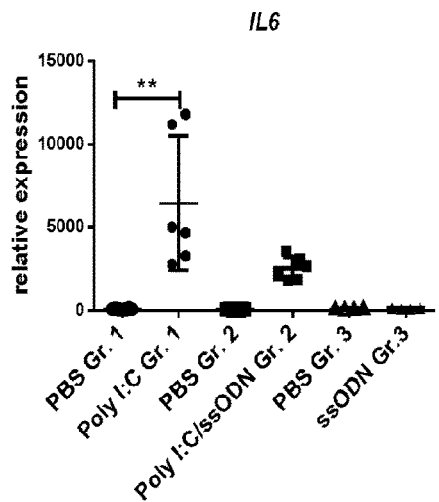
Figure 4B:
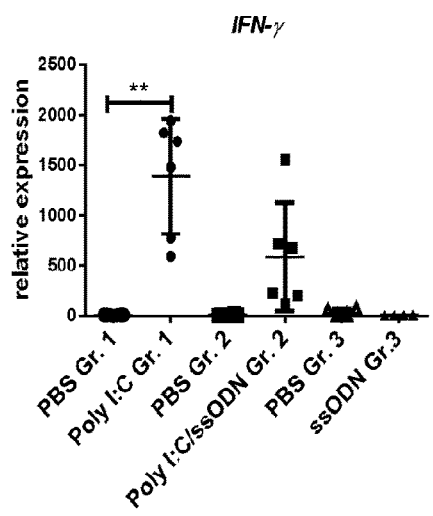
Figure 4B:
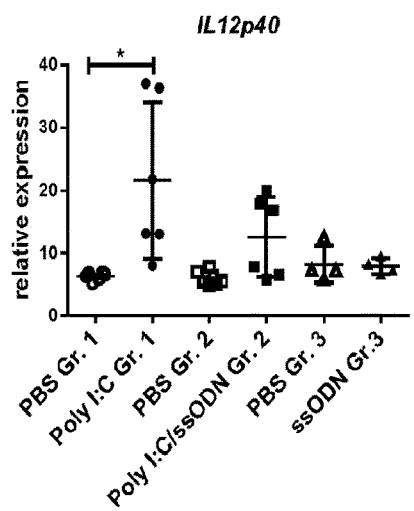

Example 4: SsON Reduces Poly(I:C)-Induced Pro-Inflammatory Cytokines and Induces IL-10 Secretion Further analysis of the molecules listed in Table I showed that Rax (the cellular activator of interferon-induced, double-stranded RNA-activated protein kinase; PKR) as well as genes implicated in inflammatory conditions such as Lrg1 and Lcn2 were significantly reduced after Poly(I:C)/ssON treatment, further adding support for ssON-mediated a dampening of inflammation (FIG. 4A). Poly(I:C) induced pro-inflammatory cytokines such as IL-6, IFN-γ and IL12p40 (FIG. 4B). However, the addition of ssON ("non-CpG 35 PS"; Table II) dampened the pro-inflammatory response, including IFN-γ which is known to regulate many chemokines [27].

Figure 5:
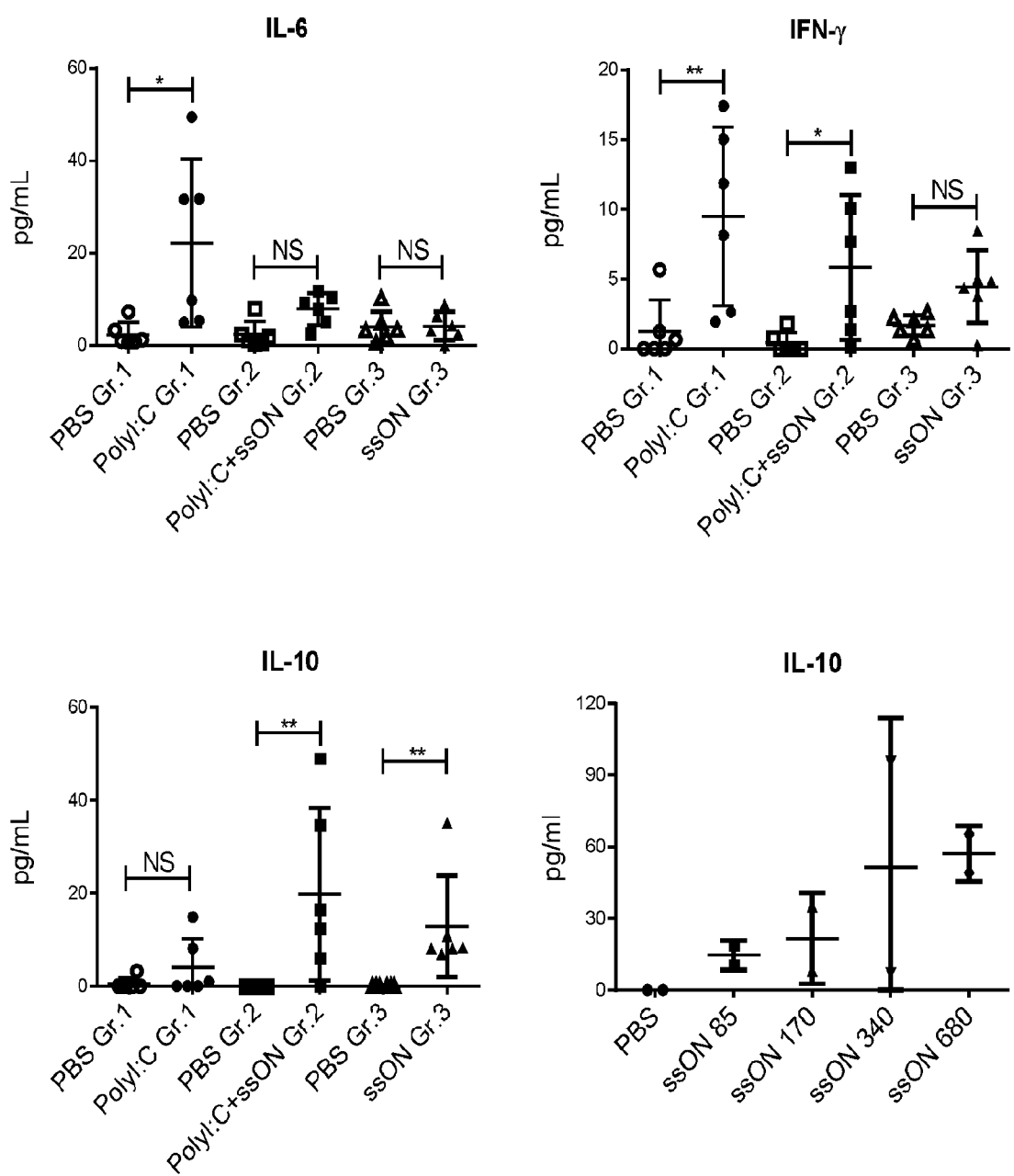
FIG. 5: The ssON treatment induces IL-10 and dampens IL-6 production in vivo. Concentrations of indicated cytokine proteins present in supernatants of enzymatically digested dermis were measured by Bio-Plex™ technology. Data are shown with means±SEM from individual animals. The lower right panel shows a dose escalation experiment with two animals treated with ssON ranging from 85 to 680 µg per injection. Significant differences were assessed by nonparametric Kruskal-Wallis test and Dunn's post-test (*$P<0.05$, $P<0.01$ and *$P<0.001$). Different treatment groups were compared using nonparametric Mann-Whitney unpaired test, as indicated (dashed arrows).

To validate whether cytokine secretion was induced in the skin, aliquots of filtered-dermis supernatants were collected and, without additional stimulation in vitro, analyzed using Bio-Plex™ analyses (FIG. 5). Significant (p<0.005) induction of IL-6 and IFN-γ was detected after Poly(I:C) treatment. There was a clear trend that addition of ssON decreased IL-6 and IFN-γ production and instead provoked significant IL-10 release. Notably, ssON alone could induce dose-dependent IL-10 secretion in vivo (FIG. 5, lower right-hand panel).

To summarize Examples 1-4, transcriptional profiling of skin biopsies revealed ssON-dependent selective dampening of dsRNA-induced pro-inflammatory responses in macaques. The ssON-modulated cytokine pattern was confirmed by protein analyses directly ex vivo from skin biopsies and revealed induction of IL-10 and inhibition of IL-6 secretion. These data demonstrate that treatment with the ssON can dampen dsRNA-induced inflammation in macaques. Moreover, the data unexpectedly show induction of IL-10 and anti-bacterial peptides after administration of ssON even without any induction of inflammation.

Example 5: Introduction of Non-Natural Linkages and Modified Nucleosides in ssONs As shown in Example 1, the 35-mer ssON denoted "nonCpG 35 PS" (SEQ ID NO: 2; Table II) with fully substituted phosphorothioate (PS) backbone, could block Poly(I:C) induced maturation of DC in a concentration dependent manner. DC maturation was monitored by measuring expression of the co-stimulatory molecules CD86 and CD80 (FIG. 1B).

Figure 6:
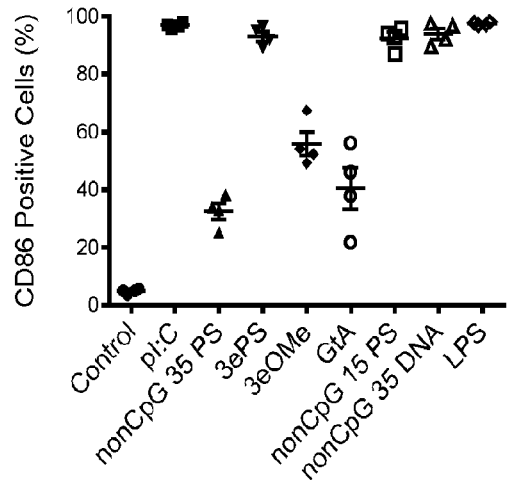
FIG. 6: Poly(I:C) induced maturation of human monocyte-derived DC. Cells treated with 25 µg/ml Poly(I:C) and 0.2 µM ssON, sequences in Table II. 100 ng/ml LPS was used as positive control. All oligonucleotide-treated cells are exposed to 25 µg/ml Poly(I:C). Mature DC markers (CD86, CD83 and CD80) were measured using flow cytometry. Experiments were performed using two donors in duplicate.
Figure 6:
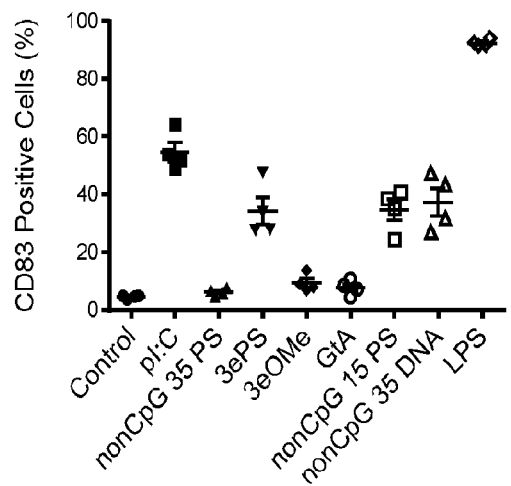
Figure 6:
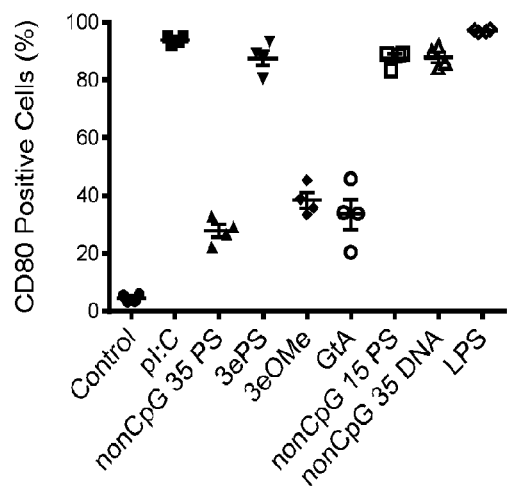

While Fully PS-substituted ssON ("nonCpG 35 PS") can block Poly(I:C) induced maturation of human monocyte-derived DCs, natural ssON with a phosphate (PO) backbone ("nonCpG 35 DNA") lost the inhibitory effect (FIG. 6). SsON efficacy was measured by monitoring the expression of DC differentiation markers CD86, CD83 and CD80.

A 35-mer ssON with three PS linkages at the 3'- and 5'-termini ("3ePS") also lacked inhibitory effect, suggesting that the PS backbone is essential for retained inhibitory effect. However, by further stabilizing the ssON by introduction of the RNA analogue 2'-O-methyl (2'OMe) in the three terminal bases ("3eOMe"), the inhibitory effect was partly restored (FIG. 6).

A PS-substituted ssON wherein all the G bases were replaced by A ("GtA") only slightly lost efficacy, showing that the sequence of fully PS-substituted ssON does not seem to influence the inhibition to a higher extent (FIG. 6).

Figure 7:
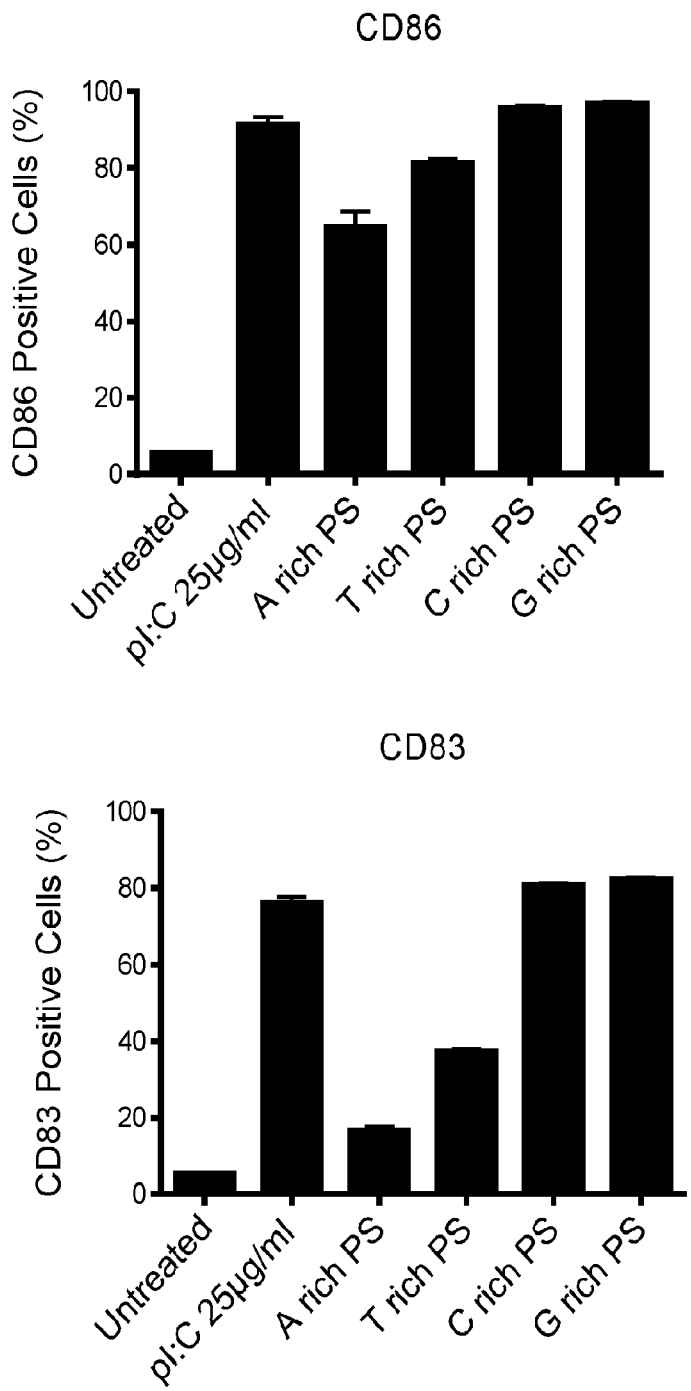
FIG. 7: Inhibitory effects on Poly(I:C) responses of human monocyte-derived DC by PS-ssONs rich in nucleobases A, T, C and G, respectively.

In experiments with different 35-mer ssONs (0.2 µM; Table III), it was shown that A- and T-rich PS-ssONs displayed inhibitory effects on Poly(I:C) induced effects (up-regulation of the co-stimulatory molecules CD86 and CD83), while C- and G-rich PS-ssONs failed to have these effects (FIG. 7).

Figure 8:
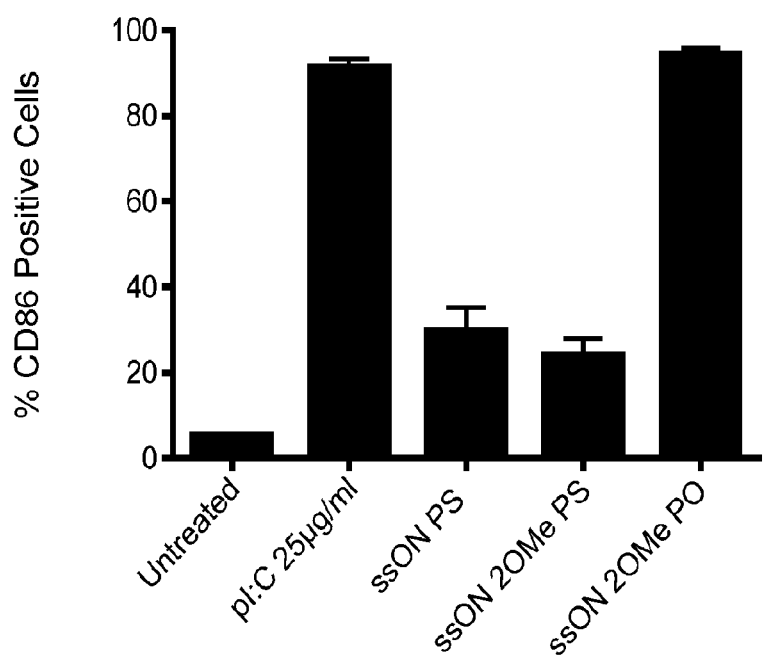
FIG. 8: Inhibitory effects on Poly(I:C) responses of human monocyte-derived DC by ssONs which were modified with 2'-O-methyl groups. The ssONs had either a phosphorothioate (PS) or a phosphodiester (PO) backbone.

The inhibitory effects on Poly(I:C) responses by ssONs which are fully modified with 2'-O-methyl (2'OMe) groups were investigated. 2'-O-methylation is a common nucleoside modification of RNA, where a methyl group is added to the 2' hydroxyl group of the ribose moiety of a nucleoside. The ssONs had either a phosphorothioate backbone ("nonCpG 2'OMe PS"; Table II) or a phosphodiester backbone ("non-CpG 2'OMe PO"; Table II). It was shown (FIG. 8) that 2'OMe could inhibit DC maturation in the same fashion as DNA if the oligonucleotide backbone was stabilized by PS linkage. A native PO backbone was less stable and the inhibitory effect was not retained.

Figure 9:
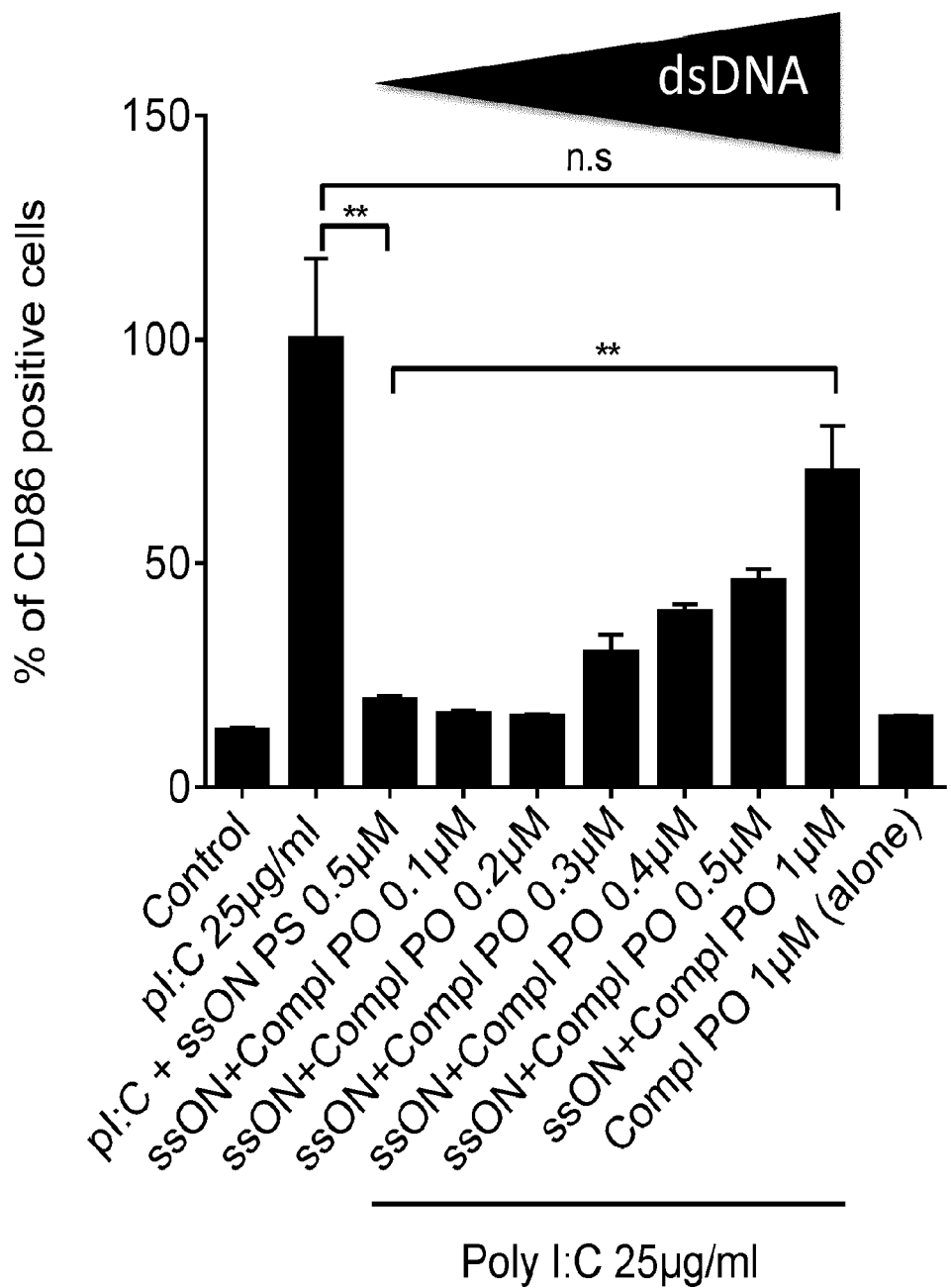
FIG. 9: Effects of increasing amounts of complementary PO DNA (allowing formation of dsDNA) on DC maturation. FACS data comes from 3 separate donors in duplicate. Error bars are given in SEM.

The effects of increasing amounts of complementary dsDNA ("nonCpG 35 DNA complementary", see Table II) on DC maturation were investigated. It was shown that dsDNA (in contrast to ssONs) does not inhibit DC maturation. Instead, addition of complementary DNA strand (increased dsDNA formation) decreased the ssON-induced inhibition of Poly(I:C) effects (FIG. 9).

Example 6: Oligonucleotide Structures

The ssONs shown in Table V were prepared as described in e.g. *Current Protocols in Nucleic Acid Chemistry* (Wiley Online Library).

Figure 10:
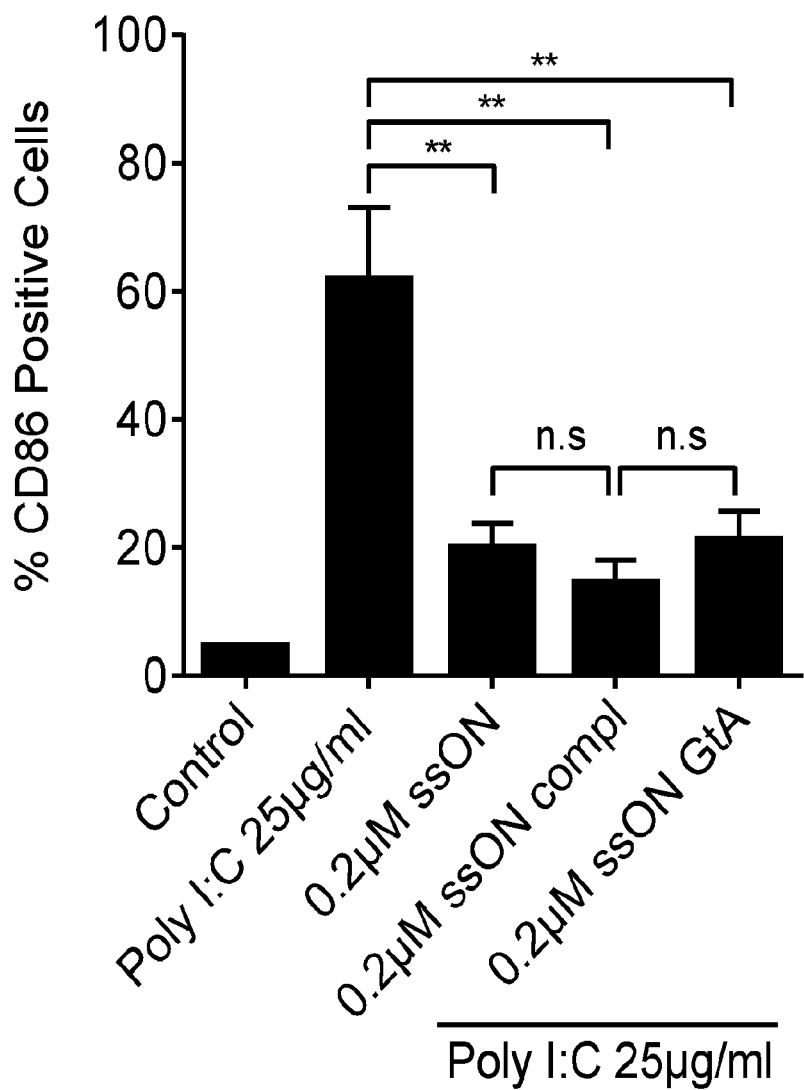
FIG. 10: Inhibitory effects on Poly(I:C) responses of human monocyte-derived DC by ssONs of the same length and (PS) backbone but different sequences.
Figure 11:
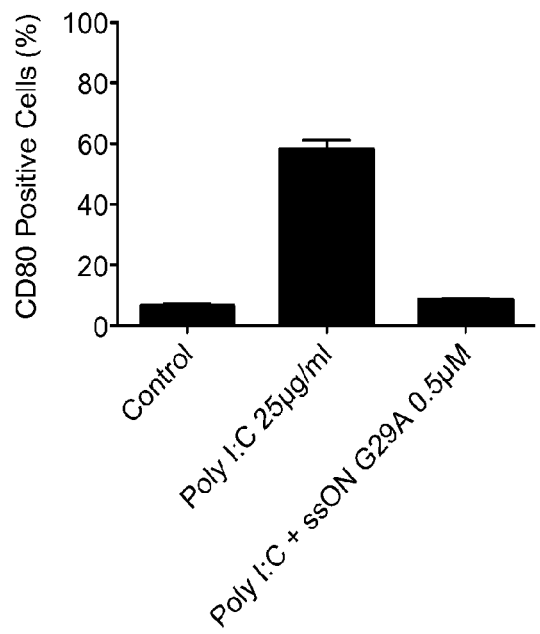
FIG. 11: Inhibitory effects on Poly(I:C) responses of human monocyte-derived DC by ssONs using a randomly mutated 35 ssON with PS backbone.
Figure 11:
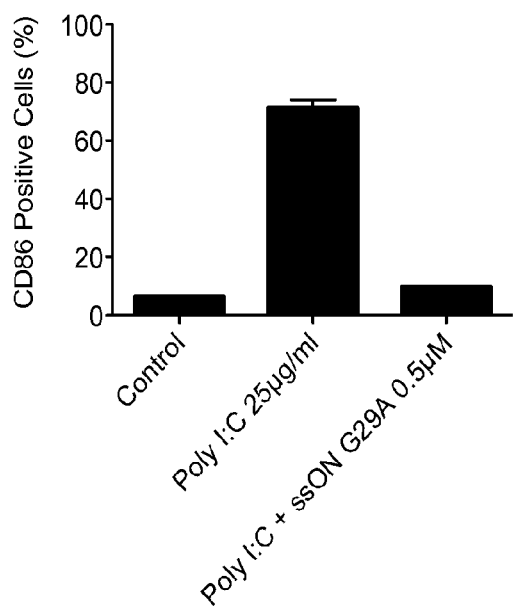
Figure 12:
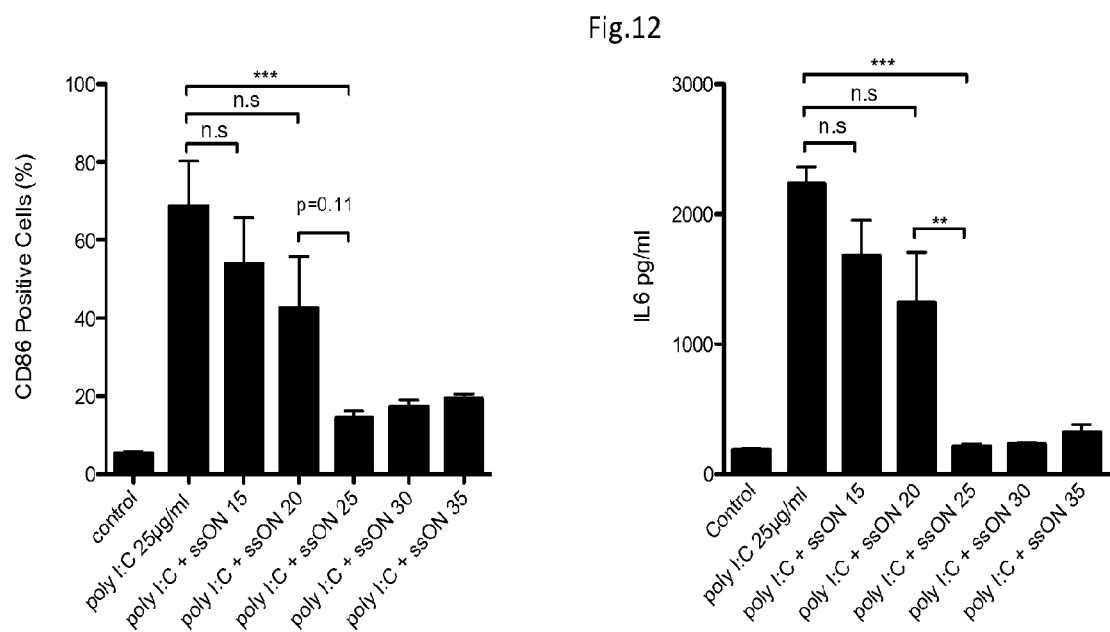
FIG. 12: Inhibitory effects on Poly(I:C) responses of human monocyte-derived DC by ssONs is length dependent. CD86 and IL-6 secretion was measured using ssONs with varying length.

The inhibitory effect seems to be independent of ssON sequence. When comparing three different ssON sequences: ssON 35 PS (SEQ ID NO: 2), ssON GtA PS (SEQ ID NO: 3), and ssON Comp1 PS (SEQ ID NO: 5) (Table V) they all display the same inhibitory effect after 48 h in monocyte-derived DCs treated with Poly(I:C) (FIG. 10). SsON GtA is based on the parent sequence ssON 35 (SEQ ID NO: 2), but all the guanosine (G) bases have been substituted to adenosine (A), while ssON Comp1 is the complementary sequence to ssON 35. The three ssONs are all 35 bases long, and have a fully PS substituted backbone. Furthermore, a random substitution of G to A at position 29 (SEQ ID NO: 19) display a similar effective inhibition of CD80 and CD86 expression in DCs as parent ssON 35 (SEQ ID NO: 2) (FIG. 11). Although sequence independent, we unexpectedly revealed a defined length-dependent requirement for inhibition of CD86 expression on DCs and release of IL-6 (FIG. 12). The shorter 30 and 25 ssONs (SEQ ID NO: 13 and 15) display similar inhibitory effect as the 35 ssON (SEQ ID NO: 2), while there was a marked reduced efficacy using 20 ssON (SEQ ID NO: 17), or 15 ssON (SEQ ID NO: 20).

Example 7: Animal Pruritus Model

Pruritic or itch responses are triggered by activation of sensory receptors expressed on primary afferents by the release of itch-inducing agents. The capacity of ssONs to influence itch in murine models recording number of scratching episodes/h is evaluated using a digital camera. Hence both the intensity and the duration of itch are measured by an observer blind to the treatment, using Ani-Tracker™ version 1.0, a software tool for analysis of animal behavior in life science.

The effect of ssONs on histaminergic/PLCβ3-induced itch is evaluated after intradermal inoculation with (a) histamine; (b) Compound 48/80, a compound that promotes histamine release; and/or (c) α-5HT (also known as α-methylserotonin); which are known to be pruritogenic.

Further, the effect of ssONs on Poly(I:C)-induced itch, and other non-histaminergic itch induced by (a) endothelin-1, which induces itch in humans and in animal models; (b) BAM (8-22) (bovine adrenal medulla 8-22 peptide, a proteolytically cleaved product of proenkephalin A) which is a potent activator of Mas-related G protein-coupled receptors (Mrgprs), MrgprC11 and hMrgprX1, and induces scratching in mice in a Mrgpr-dependent manner; (c) chloroquine, which is known to induce pruritus; and/or (d) SLIGRL, an agonist peptide derived from the N-terminus of protease-activated receptor-2 (PAR2) [14, 15]; is evaluated.

TABLE I

Top down-regulated transcripts in macaque skin after addition of ssON in vivo.

| Gene name | Ratio | FC Poly(I:C)/ssON vs Poly(I:C) | P | corr_p(BH) Poly(I:C)/ssON vs Poly(I:C) |
|---|---|---|---|---|
| CCL5 | 0.30 | −3.32 | 0.003 | 0.999 |
| CXCL9 | 0.31 | −3.23 | 0.007 | 0.999 |
| AQP4 | 0.31 | −3.19 | 0.013 | 0.999 |
| LRG1 | 0.37 | −2.69 | 0.017 | 0.999 |
| AADAC | 0.39 | −2.59 | 0.049 | 0.999 |
| UBD | 0.39 | −2.59 | 0.016 | 0.999 |
| RAX | 0.39 | −2.55 | 0.014 | 0.999 |
| IL6 | 0.39 | −2.55 | 0.040 | 0.999 |
| XIRP1 | 0.40 | −2.48 | 0.041 | 0.999 |
| FMO3 | 0.43 | −2.35 | 0.006 | 0.999 |
| IL2RA | 0.44 | −2.30 | 0.009 | 0.999 |
| LCN2 | 0.44 | −2.28 | 0.034 | 0.999 |
| RFX6 | 0.44 | −2.27 | 0.011 | 0.999 |
| PRSS2 | 0.47 | −2.15 | 0.029 | 0.999 |
| C1QC | 0.48 | −2.10 | 0.021 | 0.999 |
| CRABP1 | 0.48 | −2.09 | 0.002 | 0.999 |
| WARS | 0.48 | −2.09 | 0.028 | 0.999 |
| ICAM1 | 0.48 | −2.09 | 0.044 | 0.999 |
| CXCL11 | 0.48 | −2.06 | 0.013 | 0.999 |
| CYP11B1 | 0.50 | −2.01 | 0.011 | 0.999 |

TABLE II

Structure of oligonucleotides. All sequences are written 5' to 3'. Asterisks (*) indicate phosphorothioate linkages. Underlined letters indicate 2'-O-methyl ribose modifications; all other nucleotides are deoxynucleotides.

| Name | Sequence | Length |
|---|---|---|
| nonCpG 35 DNA (SEQ ID NO: 2) | GAAGTTTTGAGGTTTTGAAGTTGTTGGTGGTGGTG | 35 |
| nonCpG 35 PS (SEQ ID NO: 2) | G*A*A*G*T*T*T*T*G*A*G*G*T*T*T*T*G*A*A*G*T*T*G*T*T*G*G*T*G*G*T*G*G*T*G | 35 |

TABLE II-continued

Structure of oligonucleotides. All sequences are written 5' to 3'. Asterisks (*) indicate phosphorothioate linkages. Underlined letters indicate 2'-O-methyl ribose modifications; all other nucleotides are deoxynucleotides.

| Name | Sequence | Length |
| --- | --- | --- |
| 3ePS (SEQ ID NO: 2) | G*A*A*GTTTTGAGGTTTTGAAGTTGTTGGTGGTG*G*T*G | 35 |
| 3cOMe (SEQ ID NO: 2) | G*A*A*GTTTTGAGGTTTTGAAGTTGTTGGTGGTG*G*T*G | 35 |
| GtA (SEQ ID NO: 3) | A*A*A*A*T*T*T*T*A*A*A*A*T*T*T*T*A*A*A*A*T*T*A*T*T*A*A*T*A*A*T*A*A*T*A | 35 |
| nonCpG 15 DNA (SEQ ID NO: 4) | GGTTTTGAAGTTGTT | 15 |
| nonCpG 15 PS (SEQ ID NO: 4) | G*G*T*T*T*T*G*A*A*G*T*T*G*T*T | 15 |
| nonCpG 35 DNA complementary (SEQ ID NO: 5) | CACCACCACCAACAACTTCAAAACCTCAAAACTTC | 35 |
| nonCpG 2'OMe PS (SEQ ID NO: 2) | G*A*A*G*T*T*T*T*G*A*G*G*T*T*T*T*G*A*A*G*T*T*G*T*T*G*G*T*G*G*T*G*G*T*G | 35 |
| nonCpG 2'OMe PO (SEQ ID NO: 2) | GAAGTTTTGACGTTTTGAAGTTGTTGGTGGTGGTG | 35 |

TABLE III

Structure of oligonucleotides. All sequences are written 5' to 3'. Asterisks (*) indicate phosphorothioate linkages. All nucleotides are deoxynucleotides.

| Name | Sequence | Length |
| --- | --- | --- |
| A-rich PO (SEQ ID NO: 6) | AAAAAAAAAAAAAAAAAAAAAAAAAAAAAAAAAAA | 35 |
| T-rich PO (SEQ ID NO: 7) | TTTTTTTTTTTTTTTTTTTTTTTTTTTTTTTTTTT | 35 |
| C-rich PO (SEQ ID NO: 8) | CCCCCCCCCCCCCCCCCCCCCCCCCCCCCCCCCCC | 35 |
| G-rich PO (SEQ ID NO: 9) | GGGGGGGGGGGGGGGGGGGGGGGGGGGGGGGGGGG | 35 |
| A-rich PS (SEQ ID NO: 6) | A*A*A*A*A*A*A*A*A*A*A*A*A*A*A*A*A*A*A*A*A*A*A*A*A*A*A*A*A*A*A*A*A*A*A | 35 |
| T-rich PS (SEQ ID NO: 7) | T*T*T*T*T*T*T*T*T*T*T*T*T*T*T*T*T*T*T*T*T*T*T*T*T*T*T*T*T*T*T*T*T*T*T | 35 |
| C-rich PS (SEQ ID NO: 10) | C*C*C*C*T*C*C*C*C*T*C*C*C*C*T*C*C*C*C*T*C*C*C*C*T*C*C*C*C*T*C*C*C*C*T | 35 |
| G-rich PS (SEQ ID NO: 11) | G*G*G*A*A*G*G*A*A*G*G*A*A*G*G*A*A*G*G*G*A*A*G*G*A*A*G*G*G*A*A | 35 |

TABLE IV

Structure of oligonucleotides. All sequences are written 5' to 3'. All oligonucleotides are fully phosphorothioated and consists of deoxynucleotides.

| Name | Sequence | Length |
|---|---|---|
| (SEQ ID NO: 12) | GAAGTTTTGAGGTTTTGAAGTTATTGGTGGTGGTG | 35 |
| (SEQ ID NO: 13) | AGTTTTGAGGTTTTGAAGTTGTTGGTGGTG | 30 |
| (SEQ ID NO: 14) | AGTTTTGAGGTTTTGAAGTTATTGGTGGTG | 30 |
| (SEQ ID NO: 15) | TTTGAGGTTTTGAAGTTGTTGGTGG | 25 |
| (SEQ ID NO: 16) | TTTGAGGTTTTGAAGTTATTGGTGG | 25 |
| (SEQ ID NO: 17) | TGAGGTTTTGAAGTTGTTGG | 20 |
| (SEQ ID NO: 18) | TGAGGTTTTGAAGTTATTGG | 20 |
| (SEQ ID NO: 19) | GAAGTTTTGAGGTTTTGAAGTTGTTGGTAGTGGTG | 35 |
| (SEQ ID NO: 20) | GGTTTTGAAGTTGTT | 15 |

TABLE V

Explanation of ssONs used in Example 6. All oligonucleotides are fully phosphorothioated and consists of deoxynucleotides.

| Name in FIGS. 10-12 | Name in Tables II and III | SEQ ID NO: |
|---|---|---|
| ssON | nonCpG 35 PS | 2 |
| ssON compl | nonCpG 35 DNA complementary | 5 |
| ssON GtA | GtA | 3 |
| ssON G29A | — | 19 |
| ssON 15 | — | 20 |
| ssON 20 | — | 17 |
| ssON 25 | — | 15 |
| ssON 30 | — | 13 |
| ssON 35 | nonCpG 35 PS | 2 |

REFERENCES

1. Beattie, P. E., and Lewis-Jones, M. S. 2006. An audit of the impact of a consultation with a paediatric dermatology team on quality of life in infants with atopic eczema and their families: further validation of the Infants' Dermatitis Quality of Life Index and Dermatitis Family Impact score. *The British journal of dermatology* 155:1249-1255.
2. Soehnlein, O., and Lindbom, L. 2010. Phagocyte partnership during the onset and resolution of inflammation. *Nature reviews. Immunology* 10:427-439.
3. Banchereau, J., and Steinman, R. M. 1998. Dendritic cells and the control of immunity. *Nature* 392:245-252.
4. Nestle, F. O., Zheng, X. G., Thompson, C. B., Turka, L. A., and Nickoloff, B. J. 1993. Characterization of dermal dendritic cells obtained from normal human skin reveals phenotypic and functionally distinctive subsets. *Journal of immunology* 151:6535-6545.
5. Klechevsky, E., Morita, R., Liu, M., Cao, Y., Coquery, S., Thompson-Snipes, L., Briere, F., Chaussabel, D., Zurawski, G., Palucka, A. K., et al. 2008. Functional specializations of human epidermal Langerhans cells and CD14+ dermal dendritic cells. *Immunity* 29:497-510.
6. Mosser, D. M., and Zhang, X. 2008. Interleukin-10: new perspectives on an old cytokine. *Immunological reviews* 226:205-218.
7. An, H., Chandra, V., Piraino, B., Borges, L., Geczy, C., McNeil, H. P., Bryant, K., and Tedla, N. 2010. Soluble LILRA3, a potential natural antiinflammatory protein, is increased in patients with rheumatoid arthritis and is tightly regulated by interleukin 10, tumor necrosis factor-alpha, and interferon-gamma. *The Journal of rheumatology* 37:1596-1606.
8. Sköld, A. E., Hasan, M., Vargas, L., Saidi, H., Bosquet, N., Le Grand, R., Smith, C. I., and Spetz, A. L. 2012. Single-stranded DNA oligonucleotides inhibit TLR3-mediated responses in human monocyte-derived dendritic cells and in vivo in cynomolgus macaques. *Blood* 120: 768-777.
9. Saeki, H., Nakahara, T., Tanaka, A., Kabashima, K., Sugaya, M., Murota, H., Ebihara, T., Kataoka, Y., Aihara, M., Etoh, T., et al. 2016. Clinical Practice Guidelines for the Management of Atopic Dermatitis 2016. *The Journal of dermatology.*
10. Biedermann, T., Skabytska, Y., Kaesler, S., and Volz, T. 2015. Regulation of T Cell Immunity in Atopic Dermatitis by Microbes: The Yin and Yang of Cutaneous Inflammation. *Frontiers in immunology* 6:353.
11. Hamilton, J. D., Ungar, B., and Guttman-Yassky, E. 2015. Drug evaluation review: dupilumab in atopic dermatitis. *Immunotherapy* 7:1043-1058.
12. Saxena, A., Khosraviani, S., Noel, S., Mohan, D., Donner, T., and Hamad, A. R. 2015. Interleukin-10 paradox: A potent immunoregulatory cytokine that has been difficult to harness for immunotherapy. *Cytokine* 74:27-34.
13. Boniface, K., Lecron, J. C., Bernard, F. X., Dagregorio, G., Guillet, G., Nau, F., and Morel, F. 2005. Keratinocytes as targets for interleukin-10-related cytokines: a putative role in the pathogenesis of psoriasis. *European cytokine network* 16:309-319.
14. Rogoz, K., Andersen, H. H., Lagerstrom, M. C., and Kullander, K. 2014. Multimodal use of calcitonin gene-related peptide and substance P in itch and acute pain uncovered by the elimination of vesicular glutamate transporter 2 from transient receptor potential cation channel subfamily V member 1 neurons. *The Journal of neuroscience: the official journal of the Society for Neuroscience* 34:14055-14068.
15. Rogoz, K., Aresh, B., Freitag, F. B., Pettersson, H., Magnusdottir, E. I., Larsson Ingwall, L., Haddadi Andersen, H., Franck, M. C., Nagaraja, C., Kullander, K., et al. 2016. Identification of a Neuronal Receptor Controlling Anaphylaxis. *Cell reports* 14:370-379.

16. Matsukura, M., Shinozuka, K., Zon, G., Mitsuya, H., Reitz, M., Cohen, J. S., and Broder, S. 1987. Phosphorothioate analogs of oligodeoxynucleotides: inhibitors of replication and cytopathic effects of human immunodeficiency virus. *Proc Natl Acad Sci USA* 84:7706-7710.
17. Caskey, M., Lefebvre, F., Filali-Mouhim, A., Cameron, M. J., Goulet, J. P., Haddad, E. K., Breton, G., Trumpfheller, C., Pollak, S., Shimeliovich, I., et al. 2011. Synthetic double-stranded RNA induces innate immune responses similar to a live viral vaccine in humans. *J Exp Med* 208:2357-2366.
18. Ranjith-Kumar, C. T., Duffy, K. E., Jordan, J. L., Eaton-Bassiri, A., Vaughan, R., Hoose, S. A., Lamb, R. J., Sarisky, R. T., and Kao, C. C. 2008. Single-stranded oligonucleotides can inhibit cytokine production induced by human toll-like receptor 3. *Molecular and cellular biology* 28:4507-4519.
19. Zaba, L. C., Fuentes-Duculan, J., Steinman, R. M., Krueger, J. G., and Lowes, M. A. 2007. Normal human dermis contains distinct populations of CD11c+BDCA-1+ dendritic cells and CD163+FXIIIA+ macrophages. *The Journal of clinical investigation* 117:2517-2525.
20. Adar, T., Shteingart, S., Ben Ya'acov, A., Bar-Gil Shitrit, A., and Goldin, E. 2014. From airway inflammation to inflammatory bowel disease: eotaxin-1, a key regulator of intestinal inflammation. *Clinical immunology* 153:199-208.
21. Colonna, M., Navarro, F., Belton, T., Llano, M., Garcia, P., Samaridis, J., Angman, L., Cella, M., and Lopez-Botet, M. 1997. A common inhibitory receptor for major histocompatibility complex class I molecules on human lymphoid and myelomonocytic cells. *The Journal of experimental medicine* 186:1809-1818.
22. Slukvin, II, Grendell, R. L., Rao, D. S., Hughes, A. L., and Golos, T. G. 2006. Cloning of rhesus monkey LILRs. *Tissue antigens* 67:331-337.
23. Cao, W., Rosen, D. B., Ito, T., Boyer, L., Bao, M., Watanabe, G., Yao, Z., Zhang, L., Lanier, L. L., and Liu, Y. J. 2006. Plasmacytoid dendritic cell-specific receptor ILT7-Fc epsilonRI gamma inhibits Toll-like receptor-induced interferon production. *The Journal of experimental medicine* 203:1399-1405.
24. Chang, C. C., Ciubotariu, R., Manavalan, J. S., Yuan, J., Colovai, A. I., Piazza, F., Lederman, S., Colonna, M., Cortesini, R., Dalla-Favera, R., et al. 2002. Tolerization of dendritic cells by T(S) cells: the crucial role of inhibitory receptors ILT3 and ILT4. *Nature immunology* 3:237-243.
25. Banchereau, J., Zurawski, S., Thompson-Snipes, L., Blanck, J. P., Clayton, S., Munk, A., Cao, Y., Wang, Z., Khandelwal, S., Hu, J., et al. 2012. Immunoglobulin-like transcript receptors on human dermal CD14+ dendritic cells act as a CD8-antagonist to control cytotoxic T cell priming. *Proceedings of the National Academy of Sciences of the United States of America* 109:18885-18890.
26. Ali, S. R., Fong, J. J., Carlin, A. F., Busch, T. D., Linden, R., Angata, T., Areschoug, T., Parast, M., Varki, N., Murray, J., et al. 2014. Siglec-5 and Siglec-14 are polymorphic paired receptors that modulate neutrophil and amnion signaling responses to group B Streptococcus. *The Journal of experimental medicine* 211:1231-1242.
27. Antonelli, A., Ferrari, S. M., Giuggioli, D., Ferrannini, E., Ferri, C., and Fallahi, P. 2014. Chemokine (C-X-C motif) ligand $(CXCL)_{10}$ in autoimmune diseases. *Autoimmunity reviews* 13:272-280.
28. Duthie, M S, Windish, H P, Fox, C B, and Reed, S G. 2011. Use of defined TLR ligands as adjuvants within human vaccines. *Immunol Rev.* 239(1):178-96.
29. Tongaonkar, P., Trinh, K. K., Schaal, J. B., Tran, D., Gulko, P. S., Ouellette, A. J., and Selsted, M. E. 2015. Rhesus macaque theta-defensin RTD-1 inhibits proinflammatory cytokine secretion and gene expression by inhibiting the activation of NF-kappaB and MAPK pathways. *Journal of leukocyte biology* 98(6):1061-1070.
30. Lefebvre, S., and Mikkola, M. L. 2014. Ectodysplasin research—where to next? *Seminars in immunology* 26:220-228.

The invention claimed is:

1. A single-stranded oligonucleotide (ssON) for the treatment or prophylaxis of a disorder of the skin and/or subcutaneous tissue, including pruritus, wherein:
   (a) the length of the said ssON is between 25 and 70 nucleotides;
   (b) either (i) at least 90% of the internucleotide linkages in the said ssON are phosphorothioate internucleotide linkages; or (ii) the said ssON comprises at least four phosphorothioate internucleotide linkages and at least four 2'-O-methyl modifications; and
   (c) the said ssON does not contain any CpG motifs, wherein not more than 16 consecutive nucleotides in the said ssON are complementary with any human mRNA sequence, and
   wherein the said ssON is not self-complementary,
   wherein the monosaccharides in the said ssON are chosen from the group consisting of 2'-deoxyribose and 2'-O-methylribose, and
   wherein said ssON comprises the sequence shown as SEQ ID NO: 2, 12, 13, 14, 15, 16, or 19.

2. The ssON according to claim 1, wherein the said ssON comprises at least six phosphorothioate internucleotide linkages and at least six 2'-O-methyl modifications.

3. The ssON according to claim 1, wherein all internucleotide linkages in the said ssON are phosphorothioate internucleotide linkages.

4. The ssON according to claim 1, wherein the length of the said ssON is between 25 and 35 nucleotides.

5. The ssON according to claim 1, wherein said ssON comprises the sequence shown as SEQ ID NO: 19.

6. The ssON according to claim 1, wherein the said ssON is in combination with an anti-inflammatory or anti-pruritus agent.

7. A single-stranded oligonucleotide (ssON), wherein said ssON comprises the nucleotide sequence shown as SEQ ID NO: 15 or 16; provided that the ssON does not have the sequence shown as SEQ ID NO: 2.

8. The ssON according to claim 7 wherein:
   (a) the length of the said ssON is between 25 and 70 nucleotides;
   (b) either (i) at least 90% of the internucleotide linkages in the said ssON are phosphorothioate internucleotide linkages; or (ii) the said ssON comprises at least four phosphorothioate internucleotide linkages and at least four 2'-O-methyl modifications; and (c) the said ssON does not contain any CpG motifs.

9. The ssON according to claim 8 wherein the said ssON comprises at least six phosphorothioate internucleotide linkages and at least six 2'-O-methyl modifications.

10. The ssON according to claim 8 wherein all internucleotide linkages in the said ssON are phosphorothioate internucleotide linkages.

11. The ssON according to claim 7, wherein the length of the said ssON is between 25 and 35 nucleotides.

12. The ssON according to claim 7, wherein the monosaccharides in the said ssON are chosen from the group consisting of 2'-deoxyribose and 2'-O-methylribose.

13. The ssON according to claim 7, wherein said ssON has a nucleotide sequence shown as SEQ ID NO: 12, 13, 14, 15, 16, or 19.

14. A pharmaceutical composition comprising the ssON according to claim 7 together with a pharmaceutically acceptable carrier.

* * * * *